(12) United States Patent
Matsuura

(10) Patent No.: US 6,424,864 B1
(45) Date of Patent: Jul. 23, 2002

(54) METHOD AND APPARATUS FOR WAVE THERAPY

(76) Inventor: Masayuki Matsuura, 477-11, Higashimikata-cho, Hamamatsu-shi, Shizuoka-ken 433-8104 (JP)

(*) Notice: Subject to any disclaimer, the term of this patent is extended or adjusted under 35 U.S.C. 154(b) by 0 days.

(21) Appl. No.: 09/530,969
(22) PCT Filed: Nov. 27, 1998
(86) PCT No.: PCT/JP98/05342
§ 371 (c)(1),
(2), (4) Date: May 19, 2000
(87) PCT Pub. No.: WO99/27991
PCT Pub. Date: Jun. 10, 1999

(30) Foreign Application Priority Data

Nov. 28, 1997 (JP) .............................. 9-328102
Nov. 28, 1997 (JP) .............................. 9-328103

(51) Int. Cl.⁷ .............................................. A61N 1/32
(52) U.S. Cl. ................................ 607/3; 607/76; 607/66
(58) Field of Search .................................. 607/3, 66, 76

(56) References Cited

FOREIGN PATENT DOCUMENTS

| JP | 64-76876 | 3/1989 |
| JP | 1-166773 | 6/1989 |
| JP | 8-112362 | 5/1996 |
| JP | 9-94301 | 4/1997 |

*Primary Examiner*—Scott M. Getzow
(74) *Attorney, Agent, or Firm*—Arent Fox Kintner Plotkin & Kahn, PLLC

(57) ABSTRACT

An oscillator (12) of a low-frequency therapeutic apparatus (10) is controlled by a frequency control device (18) to generate a plurality of frequencies selected according to the kind of a disease and these frequencies are delivered from the lowest in an ascending order at intervals of a specified time, and are injected into a human body at the same time or separately as low-frequency electric currents from a therapeutic electrode (14) and an inactive electrode (16), as electromagnetic waves from oscillating coils (14) and (14A), and as acoustic waves from an acoustic wave oscillator (62) and a body sonic apparatus (64).

60 Claims, 14 Drawing Sheets

FIG.2

| DISEASE NAME NO. | FREQUENCY (Hz) |
|---|---|
| 001 | 19, 21, 59, 73, 94, 126, 665, 728, 739, 788, 789, 881 |
| 002 | 879, 4999, 5001, 9999, 10001 |
| 003 | 19, 61, 71, 96, 124, 667, 726, 741, 786, 791, 879, 10001 |
| 004 | 665, 728, 739, 788, 789, 881, 4999 |
| 005 ⋮ | ⋮ |

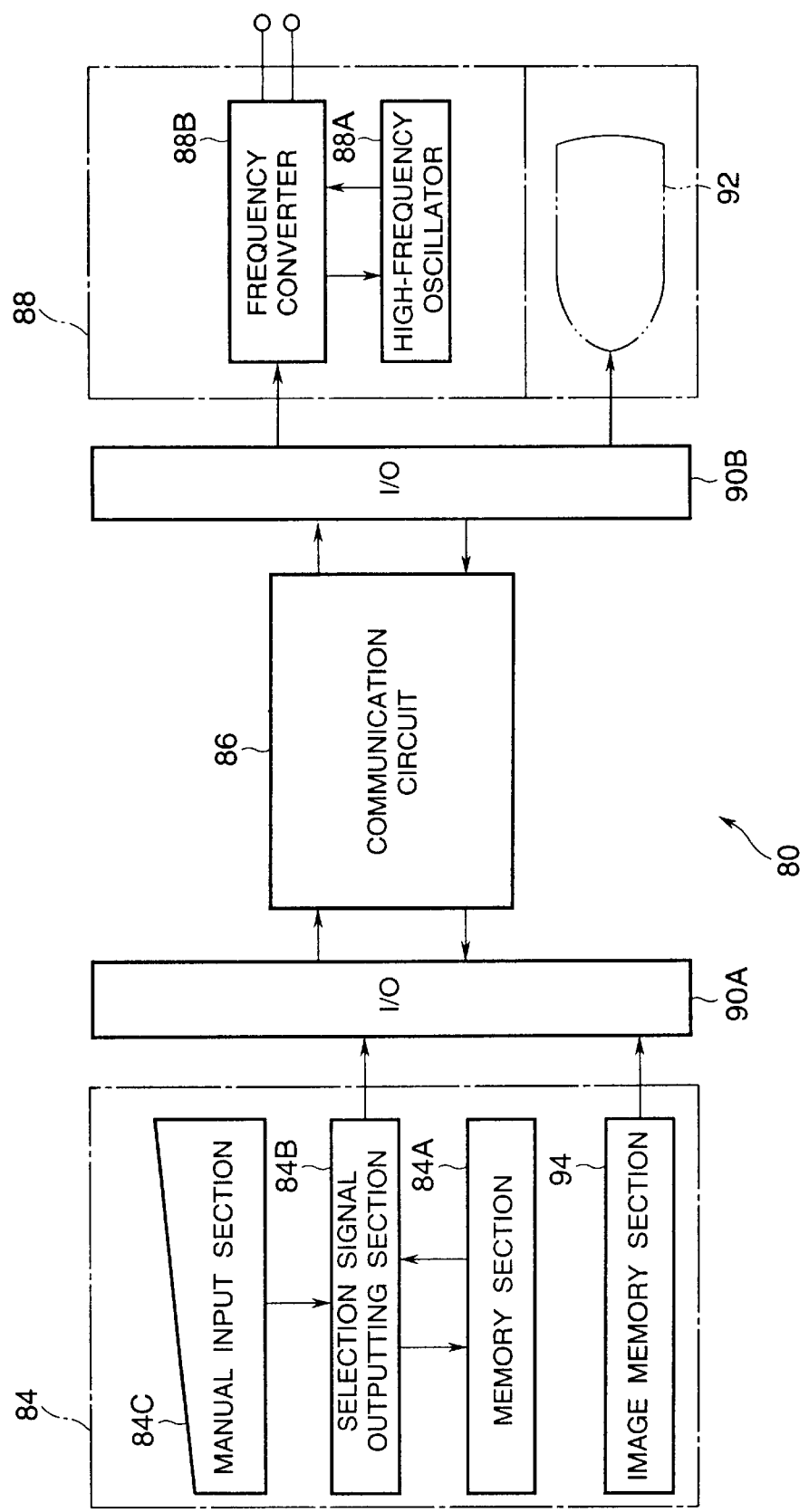

METHOD AND APPARATUS FOR WAVE THERAPY

TECHNICAL FIELD

The present invention relates to a method and an apparatus for therapy using a low-frequency electric current, electromagnetic wave and acoustic wave.

BACKGROUND ART

Conventionally, electric therapeutic machines have been used as a kind of physical therapy, and a part of the electric therapeutic machines includes a low-frequency therapeutic apparatus which aims at treating a disease by applying electrodes on the surface of the skin of a patient, and passing therewith a low-frequency current through the patient's body.

The low-frequency therapeutic apparatus comprises a therapeutic electrode (active electrode) applied on a site to be treated and an inactive electrode being opposite to the above electrode, and applies a low-frequency current between the two electrodes via a voltage delivered from an oscillator.

Such a low-frequency therapeutic apparatus is required, for example by Japanese Industrial Standards, to have an oscillator which can generate waves of at least one frequency for each of four bands of 5 Hz or lower, 5–50 Hz, 50–500 Hz and 500–1000 Hz.

Such a low-frequency therapeutic apparatus has been used for the purpose of, for example, prevention of disuse atrophy of paralyzed muscles, pain relief and recovery of failed local blood circulation, through stimulation by way of electric currents. Furthermore, particularly a small low-frequency therapeutic apparatus has been used for relaxing stiffened shoulder muscles.

The conventional low-frequency therapeutic apparatuses as described above have been exclusively used for stimulation of muscles, pain relief, and recovery of failed circulation, but remains practically ineffective for the treatment of definitive diseases.

And in the above low-frequency therapeutic apparatus, the affected part must be exposed in order to adhere an electrode to the skin of a patient, and in case of a female patient the affected part cannot be sometimes exposed, or in case of a critical patient or a disabled patient, he/she cannot sometimes take a posture to have an electrode adhered or to be treated.

DISCLOSURE OF THE INVENTION

This invention aims at providing a wave therapeutic method, apparatus and system capable of effectively treating definitive diseases by applying at least one of a low-frequency current, an electromagnetic wave and an acoustic wave.

And this invention aims at providing a wave therapeutic method, apparatus and system capable of effectively treating definitive diseases by applying a low-frequency current and/or an acoustic wave without adhering an electrode.

The present applicant previously proposed a low-frequency therapeutic method and apparatus for performing a medical treatment by passing a low-frequency current through a human body from the skin by way of Japanese Patent Laid-Open Publication No.Hei 8-137950, PCT/JP97/01849, said method and apparatus performing treatment by making the frequency of said low-frequency current higher in order at intervals of a specified time within a range of at least a part of 1 to 10000 Hz.

This method is based on the findings the present inventor has obtained themselves through experimentation. Namely, the inventor has found that, when an electric current is passed through a human body, the effective lowest frequency varies according to the kind of disease, but more or less damaged cells pass more readily the current than normal cells. To put it otherwise, an electric current of a low frequency tends to pass more readily through damaged sections within a human body. Hence, when the current passing through the patient's body is gradually increased in its frequency, the most seriously damaged parts receive the current most amply at first, which are followed step by step by less damaged parts, and thus treatment proceeds from more damaged parts to less damaged parts in order.

As for the therapeutic effect, the following assumption may be offered: if for example a cell has its membrane so sclerosed as to disrupt the interchange of intracellular and extracellular fluids, or if for example a nerve cell cannot or can scarcely transmit nerve impulses as a result of sclerosis, stimulation of the cell or nerve cell by passing a weak current whose frequency is raised step by step at specified intervals will soothe the stiffness these cells have undergone to recover their normal activity which will eventually result in the subsidence of disease or healing of the disease.

Further, the present inventor has found to make it possible to annihilate virus and bacteria by means of an electric current of a specific frequency.

And the present inventor found that electric currents having specific frequencies (for example, 69 frequencies between 1 and 10000 Hz) have a particularly notable therapeutic effect, and proposed another invention selecting in advance a plurality of frequencies from among these frequencies and performing treatment using low-frequency currents of said selected frequencies.

This is because, as different cells, muscle systems, blood vessels and lymphatics, and nervous systems are involved according to the kind of disease, it is necessary for achieving a quite satisfactory therapeutic effect to choose appropriate frequencies according to the type of cells involved in the disease of interest, and to combine those frequencies for therapy.

Said plurality of frequencies include a part of 1, 2, 4, 8, 12, 15, 20, 26, 60, 72, 95, 100, 120, 125, 160, 440, 448, 465, 500, 600, 625, 660, 666, 690, 700, 725, 727, 728, 730, 740, 770, 776, 787, 790, 799, 800, 802, 803, 804, 832, 840, 875, 878, 880, 885, 890, 1500, 1550, 1560, 1570, 1600, 1800, 1840, 1850, 1900, 1998, 2000, 2008, 2052, 2100, 2120, 2127, 2128, 2130, 2489, 2490, 3000, 5000 and 10000 Hz.

According to further experiments of the present inventors, it has been found that to make the respective frequencies higher or lower by 1 Hz than said plurality of frequencies is more effective.

And to generate an electromagnetic field by means of an electromagnetic wave of a specific frequency in the vicinity of a human body without adhering an electrode directly to the living body have made it possible to bring the same therapeutic effect as brought in case of adhering the electrode. Furthermore, it could be confirmed that the same therapeutic effect is obtained by injecting an acoustic wave of the same frequency as described above into a living body simultaneously with or separately from a low-frequency electric current or electromagnetic wave.

This invention is a wave therapeutic method for performing treatment by applying at least one of a low-frequency electric current, electromagnetic wave and acoustic wave to a living body, as described in claim 1, which method improves its therapeutic effect by selecting at least two frequencies from among 14, 16, 19, 21, 25, 27, 59, 61, 71, 73, 94, 96, 119, 121, 124, 126, 159, 161, 441, 447, 449, 464, 466, 499, 501, 599, 601, 624, 626, 659, 661, 665, 667, 689, 691, 699, 701, 724, 726, 727, 728, 729, 731, 739, 741, 769, 771, 775, 777, 786, 788, 789, 791, 799, 800, 801, 802, 803, 804, 805, 831, 839, 874, 876, 879, 881, 884, 886, 891, 1499, 1501, 1549, 1551, 1559, 1561, 1569, 1571, 1599, 1601, 1799, 1801, 1839, 1841, 1849, 1851, 1899, 1901, 1997, 1999, 2001, 2007, 2009, 2051, 2099, 2101, 2121, 2126, 2127, 2128, 2129, 2131, 2488, 2489, 2490, 2491, 2999, 3001, 4999, 5001, 9999 and 10001 Hz as the frequency of said electromagnetic wave and acoustic wave according to a disease and making the frequency higher in order at intervals of a specific time.

According to the present invention, which method performs treatment by;
first using as a basic therapy waves of 19, 61, 96, 124, 667, 726, 741, 786, 791, 879 and 10001 Hz in frequency in this order, and
next using waves having frequencies selected according to the kind of a disease.

According to the present invention, which method performs treatment by applying each of the waves having said selected frequencies to a human body for 2 to 5 minutes.

According to the present invention, a pause of 0 to 1 minute is provided when said selected frequencies are changed over.

According to the present invention, the lowest frequency of said selected frequencies is set at 14 Hz.

According to the present invention, at least two frequencies of 21, 59, 73, 94, 99, 121, 126, 447, 449, 464, 466, 499, 599, 626, 659, 667, 728, 739, 777, 788, 791, 799, 802, 805, 881, 1499, 1549, 1571, 1601, 1799. 1839, 1999, 2001, 2009, 2128, 2488, 2489, 2490, 2491, 4999 and 9999 Hz are used as said frequencies in case that a disease to be treated is acquired immunodeficiency syndrome.

According to the present invention, at least two frequencies of 667, 726, 741, 786, 791, 879, 4999 and 5001 Hz are used as said frequencies in case that a disease to be treated is allergy.

According to the present invention, at least two frequencies of 21, 61, 71, 96, 124, 665, 728, 741, 788, 791, 881, 4999, 5001, 9999 and 10001 Hz are used as said frequencies in case that a disease to be treated is arteriosclerosis.

According to the present invention, at least two frequencies of 19, 21, 59, 71, 94, 126, 667, 726, 739, 786, 791, 801, 881, 1501, 1841, 1999, 2001, 2007, 2126, 4999, 5001, 9999 and 10001 Hz are used as said frequencies in case that a disease to be treated is arthritis.

According to the present invention, at least two frequencies of 667, 728, 741, 788, 789 and 881 Hz are used as said frequencies in case that a disease to be treated is asthma.

According to the present invention, at least two frequencies of 19, 61, 96, 124, 667, 726, 741, 786, 791, 879 and 10001 Hz are used as said frequencies in case that a disease to be treated is hypotension.

According to the present invention, at least two frequencies of 19, 21, 59, 71, 94, 124, 667, 728, 739, 786, 791 and 879 Hz are used as said frequencies in case that a disease to be treated is tumor, eruption.

According to the present invention, at least two frequencies of 665, 728, 741, 777, 791 and 881 Hz are used as said frequencies in case that a disease to be treated is pneumonia.

According to the present invention, at least two frequencies of 667, 728, 741 and 879 Hz are used as said frequencies in case that a disease to be treated is bronchitis.

According to the present invention, at least two frequencies of 1999, 2001, 2007, 2009, 2126 and 2128 Hz are used as said frequencies in case that a disease to be treated is cancer (sarcoma).

According to the present invention, at least two frequencies of 2121, 2126 and 2131 Hz are used as said frequencies in case that a disease to be treated is cancer.

According to the present invention, at least two frequencies of 667, 726, 741, 788, 791, 879, 4999, 5001, 9999 and 10001 Hz are used as said frequencies in case that a disease to be treated is cataract.

According to the present invention, at least two frequencies of 665, 727, 729, 741, 788, 791, 801, 881, 4999, 5001, 9999 and 10001 Hz are used as said frequencies in case that a disease to be treated is cold, cough.

According to the present invention, at least two frequencies of 19, 61, 73, 96, 124, 667, 728, 739, 788, 789, 791, 799, 801 and 881 Hz are used as said frequencies in case that a disease to be treated is stomachache.

According to the present invention, at least two frequencies of 21, 59, 71, 94, 126, 665, 726, 741, 786, 789, 799, 801, 881, 9999 and 10001 Hz are used as said frequencies in case that a disease to be treated is colitis.

According to the present invention, at least two frequencies of 19, 59, 73, 96, 126, 667, 728, 741, 786, 789, 791, 799, 801 and 881 Hz are used as said frequencies in case that a disease to be treated is constipation.

According to the present invention, at least two frequencies of 21, 61, 71, 94, 126, 665, 739, 788, 791, 799, 801, 881, 4999, 9999 and 10001 Hz are used as said frequencies in case that a disease to be treated is cystitis.

According to the present invention, at least two frequencies of 21, 59, 73, 94, 126, 665, 728, 786, 791, 799, 881, 4999, 9999 and 10001 Hz are used as said frequencies in case that a disease to be treated is diabetes.

According to the present invention, at least two frequencies of 667, 726, 728, 741, 786, 788, 791, 879, 881, 9999 and 10001 Hz are used as said frequencies in case that a disease to be treated is duodenal ulcer.

According to the present invention, at least two frequencies of 665, 726, 728, 741, 786, 788, 789, 879 and 881 Hz are used as said frequencies in case that a disease to be treated is edema, pulmonary edema.

According to the present invention, at least two frequencies of 19, 61, 71, 94, 124, 667, 728, 741, 786, 791, 799, 801 and 881 Hz are used as said frequencies in case that a disease to be treated is influenza.

According to the present invention, at least two frequencies of 19, 21, 61, 71, 94, 124, 667, 728, 741, 788, 789, 881 and 4999 Hz are used as said frequencies in case that a disease to be treated is gallstone.

According to the present invention, at least two frequencies of 19, 21, 61, 71, 94, 124, 667, 728, 741, 788, 789, 881, 4999 and 5001 Hz are used as said frequencies in case that a disease to be treated is gallbladder.

According to the present invention, at least two frequencies of 19, 21, 61, 71, 94, 124, 667, 728, 741, 788, 789, 881, 4999, 9999 and 10001 Hz are used as said frequencies in case that a disease to be treated is gout.

According to the present invention, at least two frequencies of 19, 21, 59, 71, 96, 126, 667, 728, 741, 789, 799, 801, 879 and 881 Hz are used as said frequencies in case that a disease to be treated is hemorrhoid.

According to the present invention, at least two frequencies of 665, 726, 727, 729, 741, 791, 801, 879 and 881 Hz are used as said frequencies in case that a disease to be treated is hepatitis (inflammation of liver).

According to the present invention, at least two frequencies of 667, 726, 739, 788, 789, 4999 and 5001 Hz are used as said frequencies in case that a disease to be treated is hernia.

According to the present invention, at least two frequencies of 19, 21, 61, 73, 96, 126, 667, 728, 741, 788, 791, 881, 9999 and 10001 Hz are used as said frequencies in case that a disease to be treated is hypertension.

According to the present invention, at least two frequencies of 665, 728, 741, 788, 791, 799, 801, 881, 9999 and 10001 Hz are used as said frequencies in case that a disease to be treated is intercostal neuralgia.

According to the present invention, at least two frequencies of 665, 728, 739, 786, 791, 779, 1999, 2001, 2009, 2126 and 2128 Hz are used as said frequencies in case that a disease to be treated is leukemia and cancer.

According to the present invention, at least two frequencies of 667, 728, 741, 788, 791, 881, 9999 and 10001 Hz are used as said frequencies in case that a disease to be treated is lumbago.

According to the present invention, at least two frequencies of 19, 21, 61, 71, 96, 126, 667, 728, 741, 788, 791, 879, 881, 4999, 5001, 9999 and 10001 Hz are used as said frequencies in case that a disease to be treated is Meniere's disease.

According to the present invention, at least two frequencies of 19, 21, 61, 73, 96, 126, 667, 728, 741, 788, 791, 799, 881, 9999 and 10001 Hz are used as said frequencies in case that a disease to be treated is nephritis.

According to the present invention, at least two frequencies of 21, 61, 73, 96, 126, 667, 726, 741, 788, 879, 9999 and 10001 Hz are used as said frequencies in case that a disease to be treated is neuralgia.

According to the present invention, at least two frequencies of 667, 726, 741, 791, 879, 1501, 1601, 1839, 1999, 2001, 4999 and 5001 Hz are used as said frequencies in case that a disease to be treated is Parkinson's disease.

According to the present invention, at least two frequencies of 19, 21, 71, 94, 124, 665, 726, 741, 769, 771, 775, 777, 788, 791, 879, 881, 4999 and 5001 Hz are used as said frequencies in case that a disease to be treated is pneumonia.

According to the present invention, at least two frequencies of 19, 59, 71, 94, 124, 599, 659, 667, 728, 739, 788, 791, 801, 881, 1501, 1549, 1601, 1839, 1999, 2001, 2007, 2128, 2129, 4999, 9999 and 10001 Hz are used as said frequencies in case that a disease to be treated is rheumatism and arthritis.

According to the present invention, at least two frequencies of 665, 726, 727, 729, 739, 786, 788, 789, 879 and 881 Hz are used as said frequencies in case that a disease to be treated is laryngitis.

According to the present invention, at least two frequencies of 665, 728, 791, 801, 881, 9999 and 10001 Hz are used as said frequencies in case that a disease to be treated is calculus of kidney and gallbladder.

According to the present invention, at least two frequencies of 19, 21, 61, 73, 96, 126, 667, 728, 741, 788, 799, 801, 881 and 5001 Hz are used as said frequencies in case that a disease to be treated is tonsillitis.

According to the present invention, at least two frequencies of 19, 21, 667, 728, 741, 788, 791, 881 and 4999 Hz are used as said frequencies in case that a disease to be treated is toothache.

According to the present invention, at least two frequencies of 19, 21, 61, 71, 94, 126, 667, 728, 741, 788, 791, 799, 801, 1499, 1501, 1549, 1551, 1599 and 1601 Hz are used as said frequencies in case that a disease to be treated is tuberculosis.

According to the present invention, at least two frequencies of 19, 21, 61, 73, 96, 126, 9999 and 10001 Hz are used as said frequencies in case that a disease to be treated is whiplash.

According to the present invention, the frequencies at which electricity is passed through a living body are in a range of said selected frequencies plus or minus 3 Hz.

According to the present invention, a low-frequency current is applied between a pair of electrodes brought into contact with the skin so as to put the affected part of a living body between them.

According to the present invention, therapy is performed by arranging at least one oscillating coil of a low-frequency oscillator in the vicinity of a living body and irradiating the living body with an electromagnetic wave having a frequency in a range of at least a part of 14 to 10001 Hz through this coil as making the frequency higher in order at intervals of a specified time.

According to the present invention, the strength of an electromagnetic wave generated by said oscillating coil has a maximum of 30 V in voltage and a maximum of 50 mA in current on the cuticle of a human body in the electromagnetic field.

According to the present invention, acoustic waves of said frequencies are poured into a living body from at least one of the ears and the skin of the patient.

According to the present invention, one of said low-frequency electric current and electromagnetic wave, and said acoustic wave which are the same in frequency and synchronous with each other are injected into a living body.

An apparatus of the present invention is a wave therapeutic apparatus having at least one of a low-frequency current applying apparatus which comprises a therapeutic electrode to be attached to a site to be treated and an inactive electrode to be attached to a living body as a counterpart to said therapeutic electrode and to pass an electric current through said living body and which applies a low-frequency and low-power electric current wave between these electrodes, an electromagnetic wave applying apparatus which is provided with at least one oscillating coil capable of being arranged closely to a site to be treated of a living body and which generates an electromagnetic wave by a low-frequency current in this oscillating coil and applies the electromagnetic wave to the living body, and an acoustic wave applying apparatus which injects an acoustic wave generated by an acoustic wave oscillating device into at least one of the ears and the skin of a living body, wherein the frequencies of said waves are generated by an oscillator, said oscillator is provided with a frequency controller which selects a frequency to be oscillated from a plurality of frequencies set in advance and makes the frequency higher in order from the lower frequency side at intervals of a specific time, said frequency controller has a memory section to memorize the data of plural frequencies previously chosen appropriately in accordance with the kind of disease and a selection signal outputting section to read from the memory section the data of plural corresponding frequencies as described above in response to an instruction signal inputted in accordance with the kind of disease to be treated, and to change in order oscillation frequencies of said oscillator on the basis of the said read frequency information, and at least two frequencies of 14, 16, 19, 21, 25, 27, 59, 61, 71, 73, 94, 96, 119, 121, 124, 126, 159, 161, 441, 447, 449, 464, 466, 499, 501, 599, 601, 624, 626, 659, 661, 665, 667, 689, 691, 699, 701, 724, 726, 727, 728, 729, 731, 739, 741, 769, 771, 775, 777, 786, 788, 789, 791, 799, 800, 801, 802, 803, 804, 805, 831, 839, 874, 876, 879, 881, 884, 886, 891, 1499, 1501, 1549, 1551, 1559, 1561, 1569, 1571, 1599, 1601, 1799, 1801, 1839, 1841, 1849, 1851, 1899, 1901, 1997, 1999, 2001, 2007, 2009, 2051, 2099, 2101, 2121, 2126, 2127, 2128, 2129, 2131, 2488, 2489, 2490, 2491, 2999, 3001, 4999, 5001, 9999 and 10001 Hz are used as said plurality of frequencies.

According to the present invention, said frequencies for a basic therapy prior to treatment of each disease are set at 19, 61, 96, 124, 667, 726, 741, 786, 791, 879 and 10001 Hz.

According to the present invention, said frequencies are selected in the following manner for each disease and said memory section memorizes information of at least two frequencies of a plurality of frequencies selected for at least one kind of disease from among the following diseases.

According to the present invention, said frequencies of current to be passed through a living body are within a range of said selected frequencies plus or minus 3 Hz.

An apparatus according to the present invention is provided with said low-frequency current applying apparatus and said acoustic wave applying apparatus, wherein at least one of a therapeutic electrode and an inactive electrode in said low-frequency current applying apparatus functions also as an acoustic wave oscillator in said acoustic wave applying apparatus.

According to the present invention, said frequency controller outputs said frequency selection signal to said oscillator through a wire or wireless communication circuit.

BRIEF DESCRIPTION OF THE DRAWINGS

FIG. 2 is a table showing the content of memory stored in the memory section of the same wave therapeutic apparatus.

FIG. 20 is a block diagram showing a wave therapeutic apparatus according to a fifth embodiment of the present invention.

BEST MODE FOR CARRYING OUT THE INVENTION

Embodiments of the present invention are described in detail with reference to the drawings in the following.

Figure 1:
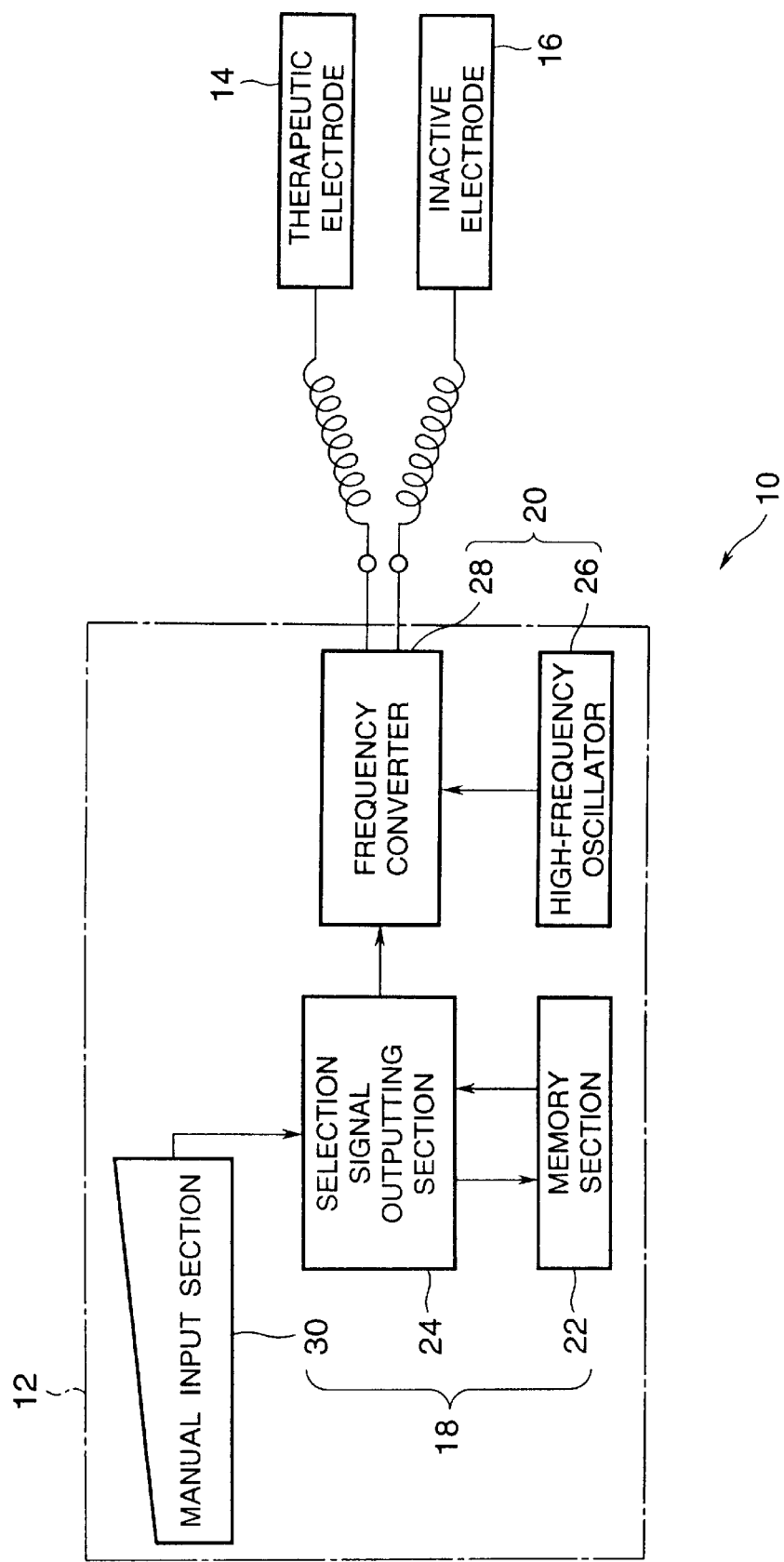
FIG. 1 is a block diagram showing a wave therapeutic apparatus according to a first embodiment of the present invention.

As shown in FIG. 1, a wave therapeutic apparatus 10 according to a first embodiment of the present invention is composed of only a low-frequency current applying apparatus 10 provided with an oscillator 12 for generating a low-power and low-frequency current, and a therapeutic electrode 14 and an inactive electrode 16 which are to be given an electric current outputted from this oscillator 12.

The therapeutic electrode 14 is an electrode to be applied to a site on a human body which requires treatment, while the inactive electrode 16 or the paired electrode to the therapeutic electrode 14, is an electrode to be applied to the same body for passage of electric current through the body.

The therapeutic and inactive electrodes 14 and 16 are composed, for example, of a conductive rubber plate or of a conductive adhesive sheet attached on the surface of a conductive rubber plate, and they can be closely attached to the surface of a human body.

The oscillator 12 comprises a frequency controller 18 to choose oscillation frequencies from among plural frequencies previously set in a range of 14 to 10001 Hz and to make them higher step by step in an ascending order at intervals of a specified time and an oscillating section 20 to oscillate the current according to control signals delivered by the frequency controller 18.

The present inventor has found through experimentation that electric currents having the following 111 frequencies in a range of 14 to 10001 Hz have a particularly notable therapeutic effect and the frequencies being in a range of these frequencies plus or minus 3 Hz have also the same therapeutic effect as described above. The other frequencies have a little therapeutic effect or no effect or a harmful effect. Said plurality of frequencies are selected from the 111 frequencies.

16, 19, 21, 25, 27, 59, 61, 71, 73, 94, 96, 119, 121, 124, 126, 159, 161, 441, 447, 449, 464, 466, 499, 501, 599, 601, 624, 626, 659, 661, 665, 667, 689, 691, 699, 701, 724, 726, 727, 728, 729, 731, 739, 741, 769, 771, 775, 777, 786, 788, 789, 791, 799, 800, 801, 802, 803, 804, 805, 831, 839, 874, 876, 879, 881, 884, 886, 891, 1499, 1501, 1549, 1551, 1559, 1561, 1569, 1571, 1599, 1601, 1799, 1801, 1839, 1841, 1849, 1851, 1899, 1901, 1997, 1999, 2001, 2007, 2009, 2051, 2099, 2101, 2121, 2126, 2127, 2128, 2129, 2131, 2488, 2489, 2490, 2491, 2999, 3001, 4999, 5001, 9999 and 10001 Hz The frequency controller 18 comprises a memory section 22 to memorize plural frequency data chosen appropriately in accordance with the kinds of diseases, a selection signal delivering section 24 to read, from the memory section 22, appropriate frequencies from among plural frequencies previously chosen as described above, in response to an instruction signal fed in accordance with the kind of disease to be treated, and to change the oscillation frequency of wave from the oscillating section 20 according to the currently read frequency data in an orderly fashion, and a manual input section 30 to be described below.

The oscillating section 20 comprises a high-frequency oscillator 26, and a frequency converter 28 which contains a demultiplier to demultiply the frequencies generated by the high-frequency oscillator 26, and converts a high frequency of electric current generated by the high-frequency oscillator 26 into a frequency corresponding to one of a plurality of predetermined frequencies in accordance with an instruction signal outputted by the selection signal outputting section 24.

The memory section 22 stores numbers representing the kinds of diseases and data of frequencies appropriate for the kinds of diseases in the form of table as presented in FIG. 2. In case of taking abscess or tumor as an example, No.001 representing the disease and appropriate frequencies to be selected comprising 19, 21, 59, 73, 94, 126, 665, 728, 739, 788, 789 and 881 Hz have been stored in memory ready for use. In case of taking stomachache as another example, No.002 representing the disease and appropriate frequencies to be selected comprising 5 frequencies in total of 879, 4999, 5001, 9999, 10001 Hz have been stored in memory. Moreover, in case that the name of a disease is pimple, No.004 representing the disease and appropriate frequencies to be selected comprising 7 frequencies in total of 665, 728, 739, 788, 789, 881 and 4999 Hz have been stored in memory.

Concretely, the frequency selection information about the following 325 kinds of diseases or damaged sites is stored:

Abscess, tumor; 19, 21, 59, 73, 94, 126, 665, 728, 739, 788, 789, 881, stomachache; 879, 4999, 5001, 9999, 10001, acidosis; 19, 61, 71, 96, 124, 667, 726, 741, 786, 791, 879, 10001, pimple; 665, 728, 739, 788, 789, 881, 4999, actinomycosis; 19, 61, 71, 96, 124, 667, 726, 741, 786, 791, 879, 891, megalgia; 879, 9999, 10001, adenoids; 19, 61, 71, 96, 124, 667, 726, 741, 786, 791, 799, 881, adhesion; 665, 728, 739, 788, 791, 881, 4999, acquired immunodeficiency syndrome; 21, 59, 73, 94, 99, 121, 126, 447, 449, 464, 466, 499, 599, 626, 659, 667, 728, 739, 777, 788, 791, 799, 802, 805, 881, 1499, 1549, 1571, 1601, 1799, 1839, 1999, 2001, 2009, 2128, 2488, 2489, 2490, 2491, 4999, 9999, alcoholism; 665, 726, 741, 786, 791, 881, 9999, 10001, allergy; 667, 726, 741, 786, 791, 879, 4999, 5001, alopecia (hair loss); 665, 728, 741, 786, 791, 879, 9999, 10001, amenorrhea (unsuccessful memses); 665, 728, 741, 788, 791, 881, 9999, 10001, anemia; 19, 61, 96, 124, 667, 726, 741, 786, 791, 879, 4999, 10001, aneurysm; 19, 21, 61, 71, 94, 126, 4999, 5001, anus (pruritus ani); 21, 59, 73, 94, 124, 726, 788, 791, 879, 9999, 10001, spleen ulceration, anthrax (infectious disease of cattle); 665, 728, 739, 788, 791, 879, disinfection, sterilization; 665, 726, 741, 786, 789, 881, 5001, appendicitis, cecitis; 667, 728, 741, 788, 791, 881, anorexia; 665, 726, 739, 786, 789, 879, 10001, AIDS-related syndrome; 626, 661, arterial sclerosis; 21, 61, 73, 95, 124, 665, 726, 741, 788, 791, 881, 4999, 9999, artery (stimulate); 665, 728, 741, 788, 791, 801, 879, 9999, 10001, arteriosclerosis; 21, 61, 71, 96, 124, 665, 728, 741, 788, 791, 881, 4999, 5001, 9999, 10001, arthritis; 19, 21, 59, 71, 94, 126, 667, 726, 739, 786, 791, 801, 881, 1501, 1841, 1999, 2001, 2007, 2126, 4999, 5001, 9999, 10001, ataxia (muscle); 665, 726, 739, 788, 791, 881, 4999, 5001, 9999, 10001, athlete's foot; 21, 59, 73, 96, 124, 665, 726, 741, 786, 791, 879, 5001, asthma; 667, 728, 741, 788, 789, 881, star-shaped cerebral or spinal cells; 665, 728, 741, 786, 789, 879, 1999, 2001, 2007, 2009, 2126, 2128, autointoxication; 665, 726, 739, 788, 791, 879, 9999, 10001, rod virus; 665, 726, 739, 786, 789, 801, 802, 804, 5001, backache; 667, 728, 741, 788, 791, 881, 9999, 10001, respiratory insufficiency; 19, 21, 61, 73, 96, 126, 4999, 5001, irritability (irritable); 667, 726, 741, 786, 789, 881, 5001, 9999, 10001, fire blister, water blister; 19, 61, 73, 96, 126, 667, 728, 739, 879, water blister, bulla; 9999, blood disease; 665, 728, 739, 786, 791, 881, hypotension; 19, 61, 96, 124, 667, 726, 741, 786, 791, 879, 10001, tumor, eruption; 19, 21, 59, 71, 94, 124, 667, 728, 739, 786, 791, 879, tumor (rash, contagion); 19, 21, 59, 73, 96, 126, 667, 728, 741, 788, 789, 881, 4999, 5001, bone (crack, fracture); 19, 61, 96, 124, 667, 726, 741, 786, 791, 879, 10001, tumor of breast; 2007, 2127, 2129, region of chest; 19, 61, 96, 124, 667, 726, 741, 786, 791, 879, 4999, 10001, respiration; 19, 61, 96, 124, 667, 726, 741, 786, 791, 879, 5001, 10001, Bright's disease (most dangerous nephritis), nephritis; 667, 726, 739, 788, 791, 801, 879, pneumonia; 665, 728, 741, 777, 791, 881, bronchitis; 667, 728, 741, 879, bruise, cut, contusion; 667, 726, 741, 791, 881, 9999, 10001, bubonic plague, contagious disease; 19, 61, 73, 94, 124, 499, 501, 4999, pain of hallux valgus; 19, 21, 61, 73, 94, 124, 667, 726, 739, 788, 791, 4999, 5001, burn (radiant heat); 2126, 9999, 10001, burn (heat); 19, 61, 96, 124, 667, 726, 741, 786, 791, 879, 10001, bursitis; 665, 726, 739, 786, 791, 881, butterfly-shaped erythematous lupus; 665, 728, 739, 775, 777, 788, 791, 1841, 1849, cancer (sarcoma); 1999, 2001, 2007, 2009, 2126, 2128, cancer (generally, for prevention); 1997, 1999, cancer (inside, outside); 2126, cancer (leukemia); 9, 61, 96, 124, 667, 726, 741, 786, 791, 879, 2128, 10001, noma; 19, 59, 73, 96, 124, 665, 728, 741, 788, 791, 801, 881, 4999, 5001, mycosis fungoides, cavernous hemangioma, cutaneous disease of fish; 466, 2128, pimple, eruption; 21, 61, 73, 94, 126, 667, 728, 739, 788, 791, 881, 4999, 5001, cancer; 2121, 2126, 2131, heart disease (sedative effect); 665, 728, 739, 786, 789, 881, 4999, 5000, 9999, 10001, cataract; 667, 726, 741, 788, 791, 879, 4999, 5001, 9999, 10001, catarrh (inflammation of nasal mucous membrane); 19, 21, 59, 73, 96, 124, 665, 726, 741, 788, 789, 879, cerebral infantile paralysis; 665, 726, 739, 788, 791, 881, 9999, 10001, cerebrospinal meningitis; 667, 728, 741, 786, 789, 879, 9999, 10000, gland of neck (wen, swelling); 667, 728, 741, 786, 789, 879, 4999, 5001, cervicitis; 19, 59, 73, 96, 124, 665, 728, 741, 788, 791, 879, chicken pox, 19, 21, 61, 71, 94, 126, 667, 728, 739, 786, 789, 881, chilblains, frostbite; 19, 21, 59, 73, 96, 126, 4999, 5001, psychomatic disorder; 65, 728, 881, poor circulation (foot); 19, 21, 61, 73, 94, 124, 4999, 5001, poor circulation (hand); 19, 21, 59, 71, 96, 126, 4999, 5001, cold, cough; 665, 727, 729, 741, 788, 791, 801, 881, 4999, 5001, 9999, 10001, cold (head); 665, 727, 729, 739, 786, 789, 881, 4999, 5001, stomachache; 19, 61, 73, 96, 124, 667, 728, 739, 788, 789, 791, 799, 801, 881, colitis (mucosa of colon); 21, 59, 71, 94, 126, 665, 726, 741, 786, 789, 799, 801, 881, 9999, 10001, conjunctivitis (expansion of eyelid); 665, 726, 727, 729, 741, 788, 789, 801, 881, constipation; 19, 59, 73, 96, 126, 667, 728, 741, 786, 789, 791, 799, 801, 881, contraction of swelling, oozing of pus; 21, 61, 71, 94, 124, 665, 726, 788, 791, 881, 9999, 10001, spasm, convulsion; 665, 726, 739, 786, 791, 879, 4999, 9999, 10001, corn; 19, 21, 61, 71, 94, 126, 667, 726, 741, 788, 791, 879, 4999, 9999, 10001, coryza; 667, 726, 739, 788, 791, 881, costalgia; 667, 728, 739, 788, 791, 879, 5001, 9999, 10001, convulsion, leg cramp; 665, 726, 741, 788, 789, 881, 4999, 9999, 10001, cut (speed remedy); 19, 21, 59, 73, 96, 126, 667, 728, 741, 788, 791, 881, 4999, 5001, 9999, cystitis; 21, 61, 71, 94, 126, 665, 739, 788, 791, 799, 801, 881, 4999, 9999, 10001, dandruff; 21, 61, 71, 94, 126, 667, 728, 741, 788, 791, 881, 4999, 5001, deafness; 19, 21, 59, 73, 96, 126, 667, 739, 788, 789, 799, 801, 881, 4999, 9999, 10001, discouragement, melancholy; 9999, detoxification; 19, 61, 71, 94, 126, diabetes; 21, 59, 73, 94, 126, 665, 728, 786, 791, 799, 881, 4999, 9999, 10001, diarrhea (dysentery); 665, 728, 739, 788, 789, 801, 879, 4999, 5001, digestive power; 667, 726, 741, 786, 791, 879, 4999, 5001, diphtheria; 19, 21, 61, 71, 96, 124, 667, 726, 728, 739, 786, 788, 791, 879, 881, swelled organ; 21, 59, 73, 94, 126, 665, 728, 739, 788, 789, 881, 9999, 10001, swelled stomach; 667, 726, 741, 786, 791, 799, 801, 879, 4999, 5001, vertigo; 19, 21, 61, 71, 96, 124, 9999, 10001, edema; 665, 728, 786, 791, 9999, 10001, medicinal poisoning; 19, 21, 59, 73, 94, 126, 665, 728, 739, 788, 789, 881, 4999, 9999, 10001, duodenal ulcer; 667, 726, 728, 741, 786, 788, 791, 879, 881, 9999, 10001, dysmenorrhea (menorrhalgia); 665, 726, 728, 739, 788, 789, 799, 879, 881, indigestion, dyspepsia; 667, 726, 741, 786, 791, 799, 801, 881, colon bacillus; 791, 798, 800, 801, 802, 803, 805, ear; 19, 21, 59, 73, 94, 126, 879, 881, 4999, 5001, 9999, eczema; 667, 726, 741, 1499, 1501, 1549, 1551, 4999, pulmonary edema; 665, 726, 728, 741, 786, 788, 789, 879, 881, expanded gland; 19, 61, 71, 96, 124, 667, 726, 741, 786, 791, 9999, 10001, nocturnal enuresis; 667, 726, 741, 786, 791, 9999, 10001, epididymitis, epididymitis; 19, 21, 59, 73, 94, 126, 665, 728, 739, 788, 789, 881, 1499, 1501, epilepsy; 19, 21, 61, 71, 96, 119, 121, 124, 728, 739, 788, 789, 879, EB virus; 464, 466, 659, 661, 667, 726, 741, 786, 791, 879, 1999, 2001, 2007, 2126, 2128, erysipelas (cutaneous inflammation); 21, 59, 73, 94, 126, 599, 601, 661, 667, 728, 741, 788, 791, 1997, 1999, 2001, 2009, gullet; 665, 728, 741, 788, 791, 881, auditory tube, nose, ear; 19, 21, 61, 71, 96, 124, 667, 726, 741, 786, 791, 799, 801, 881, eyestrain; 728, 788, 879, eye (whole); 19, 21, 61, 73, 94, 126, 4999, 5001, 9999, 10001, facial paralysis; 665, 726, 739, 788, 881, 4999, 5001, 9999, 10001, facial spasm; 667, 728, 741, 786, 791, 879, 9999, 10001, fainting, swoon; 19, 21, 61, 71, 94, 126, 665, 728, 739, 788, 789, 881, 4999, 5001, fascia, muscle sheath; 19, 21, 59, 73, 96, 124, 667, 726, 741, 786, 791, 879, 4999, 5001, fatigue; 665, 739, 791, 1841, 1999, 9999, 10001, fever (in general); 19, 21, 59, 71, 96, 126, 665, 728, 741, 788, 791, 881, 4999, 5001, crack of rectum; 19, 21, 61, 73, 94, 124, 667, 726, 739, 786, 789, 879, 9999, 10001, fistulation, fistula (rectum ulcer), 667, 726, 741, 788, 791, 879, gas in the stomach and intestines; 667, 728, 741, 788, 791, 799, 801, 881, 4999, 5001, influenza; 19, 61, 71, 94, 124, 667, 728, 741, 786, 791, 799, 801, 881, sitotoxism; 667, 726, 739, 788, 791, 879, 9999, 10001, foot (ordinary injury); 665, 728, 739, 788, 791, 881, 9999, 10001, frostbite; 665, 728, 741, 788, 791, 879, 4999, 5001, gallstone; 19, 21, 61, 71, 94, 124, 667, 728, 741, 788, 789, 881, 4999, gallbladder; 19, 21, 61, 71, 94, 124, 667, 728, 741, 788, 789, 881, 4999, 5001, gangrene; 19, 21, 667, 726, 728, 741, 786, 788, 789, 879, 881, 4999, gastritis; 19, 21, 61, 73, 96, 124, 667, 728, 741, 788, 789, 881, 4999, 5001, all glands; 19, 21, 61, 73, 96, 126, 728, 741, 788, 789, 879, 9999, 10001, glaucoma; 19, 61, 96, 124, 667, 726, 741, 786, 791, 879, 1601, 10001, goiter; 19, 21, 59, 71, 96, 126, 667, 728, 741, 788, 791, 881, 4999, 5001, 9999, 10001, genital gland (inflammation); 667, 726, 728, 741, 786, 788, 791, 879, 881, 4999, gonorrhea, 599, 601, 659, 661, 667, 699, 701, 728, 741, 788, 789, 881, 4999, gout, 19, 21, 61, 71, 94, 124, 667, 728, 741, 788, 789, 881, 4999, 9999, 10001, gravel (deposits in urine); 667, 728, 739, 786, 789, 879, 4999, 5001, gingival inflammation; 19, 21, 61, 73, 94, 124, 791, 799, 801, 881, 4999, 5001, 9999, 10001, damaged hair; 19, 21, 59, 71, 94, 126, 667, 728, 741, 791, 801, 881, 9999, 10001, hallucination, 19, 21, 61, 73, 96, 124, 665, 726, 741, 788, 881, 4999, 5001, 9999, hangover; 19, 61, 96, 124, 667, 726, 741, 786, 791, 879, 9999, 10001, hay fever; 665, 728, 741, 788, 791, 881, 4999, 5001, head (oppression); 19, 21, 61, 73, 96, 124, 665, 726, 739, 788, 791, 879, 4999, 5001, headache; 19, 21, 61, 73, 96, 124, 667, 726, 741, 788, 791, 881, 9999, 10001, heart (in general); 665, 728, 741, 788, 791, 881, 4999, 5001, 9999, hemorrhage; 801, 9999, hemorrhoid; 19, 21, 59, 71, 96, 126, 667, 728, 741, 789, 799, 801, 879, 881, hepatitis (inflammation of liver); 665, 726, 727, 729, 741, 791, 801, 879, 881, hernia of an intervertebral disk; 665, 728, 741, 788, 791, 9999, 10001, hernia; 667, 726, 739, 788, 789, 4999, 5001, herpes (zoster blister); 665, 728, 741, 788, 879, 1549, 1551, 1841, 1849, 1851, 1899, 1901, 1997, 2001, 2007, hiccough; 19, 21, 59, 73, 94, 124, 9999, 10001, pain of hip; 19, 59, 71, 94, 124, 665, 728, 741, 788, 791, 881, 4999, 5001, urticaria; 667, 728, 741, 788, 791, 881, 1799, 1801, 4999, hoarse voice; 665, 726, 728, 741, 786, 788, 789, 879, 881, hot flash; 19, 61, 96, 124, 667, 726, 741, 786, 791, 879, 9999, 10001, edema; 667, 728, 741, 788, 791, 881, 9999, 10001, gastric hyperacidity; 19, 21, 61, 73, 96, 126, 667, 728, 741, 788, 791, 881, 9999, 10001, hypertension; 19, 21, 61, 73, 96, 126, 667, 728, 741, 788, 791, 881, 9999, 10001, hypochondriasis (melancholia); 19, 21, 61, 73, 96, 126, 667, 728, 741, 788, 791, 881, 9999, 10001, dyspnea, hypoxia; 667, 728, 741, 788, 791, 881, 9999, 10001, inflammation of colon; 19, 59, 71, 96, 126, 667, 728, 741, 788, 791, 799, 801, 881, asthenia, inertia; 19, 61, 96, 124, 667, 726, 741, 786, 791, 879, 9999, 10001, gigantism; 19, 61, 96, 124, 667, 726, 741, 786, 791, 879, 999910001, indigestion, dyspepsia; 665, 728, 741, 788, 791, 881, 4999, 5001, infantile paralysis; 667, 728, 741, 788, 791, 881, 1499, 1501, 1551, 1599, 1841, 1999, contagious disease; 19, 21, 726, 728, 729, 741, 788, 791, 881, inflammation of breast; 665, 728, 739, 786, 789, 881, 4999, 5001, influenza, influenza; 19, 21, 61, 73, 96, 124, 665, 726, 741, 788, 791, 799, 801, 879, 881, injury; 4999, 5001, 9999, sting of an insect; 665, 726, 728, 741, 788, 791, 879, 881, insomnia; 667, 728, 739, 788, 791, 881, 9999, 10001, intelligence, intellectuality (for improvement); 19, 21, 61, 73, 94, 124, 9999, 10001, intercostal neuralgia; 665, 728, 741, 788, 791, 799, 801, 881, 9999, 10001, intestines (inflammation); 667, 726, 741, 788, 789, 881, intestines (spasm); 665, 728, 741, 788, 791, 799, 801, 4999, 5001, intestines (in general); 665, 728, 741, 788, 789, 799, 801, 881, drunkenness, excitation; 19, 61, 96, 124, 667, 726, 741, 786, 791, 879, 9999, 10001, irritable, quick temper; 19, 21, 59, 73, 94, 124, 4999, 5001, 9999, 10001, urtication of anus; 667, 728, 741, 788, 789, 881, 4999, 5001, jaundice; 667, 728, 741, 788, 791, 881, 4999, 5001, joint (inflammation in general); 667, 728, 741, 788, 791, 881, 9999, 10001, kidney (general); 19, 21, 59, 71, 94, 124, 665, 728, 788, 791, 881, 9999, 10001, pain in knee; 21, 61, 71, 96, 126, 667, 728, 741, 788, 791, 799, 801, 881, 9999, promotion of secretion of breast milk; 19, 61, 96, 124, 667, 726, 741, 786, 791, 879, 4999, 10001, languidness, fatigue, weakness; 19, 21, 59, 71, 94, 124, 665, 728, 788, 791, 881, chronic diarrhea; 19, 61, 73, 96, 124, 667, 728, 741, 788, 791, 799, 801, 881, Hansen's disease; 599, 601, 667, 726, 739, 777, 791, 881, 9999, 10001, leukocyte; 19, 59, 73, 96, 126, 667, 728, 741, 4999, 5001, leukemia and cancer; 665, 728, 739, 786, 791, 779, 1999, 2001, 2009, 2126, 2128, abnormal secretion of white discharge from the vagina; 665, 726, 728, 741, 786, 788, 791, 879, 881, whole liver; 665, 726, 727, 729, 739, 786, 788, 789, 791, 881, motor ataxia; 667, 728, 741, 788, 791, 881, 9999, 10001, lumbago; 667, 728, 741, 788, 791, 881, 9999, 10001, crooked waist vertebra; 667, 728, 741, 788, 791, 881, 9999, 10001, lupus; 1499, 1549, 1551, 1601, 1841, 1997, whole lymphatic tissue; 665, 728, 741, 788, 791, 881, 4999, 5001, malaria; 19, 21, 59, 71, 94, 126, measles; 665, 726, 727, 729, 741, 786, 788, 791, 879, 881, depression; 19, 61, 96, 124, 667, 726, 741, 786, 791, 879, 4999, 10001, memory; 19, 21, 59, 71, 94, 124, 9999, 10001, Meniere's disease; 19, 21, 61, 71, 96, 126, 667, 728, 741, 788, 791, 879, 881, 4999, 5001, 9999, 10001, meningitis, meningoencephalitis; 19, 21, 61, 73, 96, 126, 4999, 5001, missed period; 665, 728, 741, 788, 791, 881, 9999, 10001, menorrhalgia; 19, 25, 27, 61, 73, 96, 126, mental retardation; 19, 21, 59, 73, 96, 124, 9999, 10001, migraine; 19, 21, 665, 728, 741, 879, 791, 881, 4999, 5001, Down's syndrome; 21, 4999, stomatitis; 19, 21, 59, 71, 94, 124, 665, 726, 741, 788, 791, 881, 4999, disease of evacuation; 19, 9999, multiple sclerosis; 19, 59, 71, 94, 124, 665, 726, 739, 788, 789, 879, 4999, 5001, epidemic parotiditis; 665, 726, 727, 729, 741, 786, 788, 791, 879, 881, muscles (restoration); 19, 61, 96, 124, 667, 726, 741, 786, 791, 879, 4999, 10001, muscular dystrophy; 665, 726, 739, 788, 791, 881, 4999, 5001, nausea, vomiturition; 667, 728, 741, 788, 791, 881, 4999, 5001, whole neck; 19, 59, 71, 96, 124, 667, 728, 741, 788, 791, 881, 4999, 5001, nephritis; 19, 21, 61, 73, 96, 126, 667, 728, 741, 788, 791, 799, 881, 9999, 10001, dental neuritis; 667, 728, 741, 788, 791, 881, 9999, 10001, erethism (sedative effect); 4999, neuralgia; 21, 61, 73, 96, 126, 667, 726, 741, 788, 879, 9999, 10001, nervous prostration (fatigue); 665, 726, 739, 786, 791, 881, 4999, 5001, neuritis; 665, 726, 739, 786, 791, 881, 9999, 10001, neurosis; 665, 726, 739, 786, 791, 881, 9999, 10001, nicotinism; 19, 61, 96, 124, 667, 726, 741, 786, 791, 879, 9999, 10001, nasal disorder; 665, 726, 728, 739, 786, 788, 791, 881, adiposis; 19, 61, 96, 124, 667, 726, 741, 786, 791, 879, 9999, 10001, occipital neuralgia; 19, 61, 73, 94, 124, 665, 726, 739, 788, 791, 881, 4999, 5001, testitis; 665, 728, 741, 788, 791, 799, 799, 801, 881, arthritis; 665, 728, 741, 788, 791, 881, 1499, 1501, 1551, 1601, 1839, 1999, osteomyelitis; 665, 728, 741, 788, 791, 881, 4999, 5001, whole ovary; 726, 788, 881, pain, ache; 665, 728, 739, 786, 789, 881, 1841, 1999, Parkinson's disease; 667, 726, 741, 791, 879, 1501, 1601, 1839, 1999, 2001, 4999, 5001, pancreas; 14, 16, 19, 61, 73, 94, 124, 665, 728, 739, 788, 791, 881, parasite; 19, 73, 96, 119, 121, 126, 439, 441, 447, 665, 726, 739, 786, 791, 799, 881, parathyroid; 665, 726, 728, 741, 786, 788, 791, 879, 881, whole pelvis; 19, 21, 61, 71, 96, 126, 659, 661, 665, 728, 741, 788, 791, 881, 1499, 1501, 1551, 1599, 1841, 1999, pericarditis; 665, 726, 728, 741, 786, 788, 791, 879, 881, periodontal disease; 665, 726, 728, 741, 786, 788, 791, 879, 881, tonic disease; 19, 21, 61, 71, 94, 119, 121, 124, 4999, laryngitis; 667, 726, 728, 741, 786, 788, 791, 879, 881, hemorrhoids; 19, 21, 61, 71, 94, 124, 788, 791, 799, 801, 879, 881, threadworm, parasite; 19, 21, 61, 73, 96, 119, 121, 124, 788, 791, 799, 801, placenta (afterbirth); 665, 726, 728, 741, 786, 788, 791, 879, 881, blood plasma, lymphoid plasma (cleaning); 19, 61, 96, 124, 667, 726, 741, 786, 791, 879, 4999, 10001, pleurisy, (pleura); 19, 21, 59, 71, 94, 124, 665, 726, 741, 789, 879, 4999, 5001, pneumonia; 19, 21, 71, 94, 124, 665, 726, 741, 769, 771, 775, 777, 788, 791, 879, 881, 4999, 5001, poison (drug), botulism, ptomaine toxication, narcotic; 9999, acute anterior poliomyelitis; 665, 728, 741, 788, 791, 879, 1499, 1501, 1551, 1601, 1839, 1999, polyp (nasal polyp); 1841, 1999, 2001, 2126, 2127, 2129, prostatitis; 665, 726, 741, 788, 791, 879, 4999, psoriasis; 19, 21, 61, 71, 94, 124, 665, 726, 739, 788, 791, 881, 4999, 5001, blepharoptosis; 665, 726, 739, 788, 791, 881, 4999, 9999, pyorrhea; 19, 21, 59, 71, 94, 124, 665, 726, 739, 788, 791, 4999, rabies, hydrophobia; 19, 21, 59, 71, 94, 119, 121, 126, 665, 728, 741, 788, 791, 879, rheumatism; 665, 728, 741, 788, 791, 879, 9999, 10001, rheumatism and arthritis; 19, 59, 71, 94, 124, 599, 659, 667, 728, 739, 788, 791, 801, 881, 1501, 1549, 1601, 1839, 1999, 2001, 2007, 2128, 2129, 4999, 9999, 10001, nasal catarrh; 19, 21, 61, 71, 96, 119, 121, 126, 667, 728, 741, 788, 881, rachitis; 19, 61, 96, 124, 667, 726, 741, 786, 791, 879, 4999, 10001, tinea, ringworm; 19, 21, 59, 71, 94, 119, 121, 124, 788, 791, 799, 801, sarcoma; 1997, 1999, 2001, 2009, 2099, 2101, 2126, 2127, scarlet fever; 665, 726, 727, 729, 739, 786, 788, 791, 879, 881, sciatic neuralgia; 19, 21, 59, 71, 94, 119, 121, 124, 665, 726, 739, 788, 791, 881, scorbutus; 19, 61, 96, 124, 667, 726, 741, 786, 791, 879, 4999, 10001, hemiplegia; 19, 21, 59, 71, 94, 126, 4999, 5001, zoster; 1501, 1549, 1551, 1601, 1839, 1999, 2001, sinus fistula; 19, 21, 59, 71, 96, 119, 121, 124, 665, 726, 739, 788, 789, 881, sinusitis; 665, 726, 728, 741, 786, 788, 791, 879, 881, cutis (hemorrhage); 786, 791, 799, 801, 4999, 5001, 9999, sleeping sickness; 19, 21, 59, 71, 96, 119, 121, 126, 667, 728, 741, 788, 791, 881, dislocation of an intervertebral disk; 665, 728, 739, 788, 789, 9999, 10, 001, variola, smallpox; 667, 726, 727, 729, 741, 786, 788, 791, 879, 881, smell (lack, deficiency); 19, 21, 59, 71, 96, 126, 9999, 10001, diseased smell; 665, 728, 739, 788, 791, 799, 801, sneeze; 665, 728, 739, 788, 789, 881, 9999, 10001, laryngitis; 665, 726, 727, 729, 739, 786, 788, 789, 879, 881, muscular spasm; 19, 21, 59, 71, 94, 124, 9999, 10001, unconscious spermatorrhea; 19, 21, 59, 71, 94, 124, 9999, 10001, spleen (hypertrophy); 19, 21, 61, 71, 94, 126, spondylitis; 788, 789, 799, 801, 879, 881, 1549, 1559, 1561, 1571, sprain, wrick in general; 19, 21, 59, 71, 94, 126, 4999, 5001, dysphemia; 19, 21, 59, 71, 96, 126, 665, 728, 741, 788, 791, 881, 9999, 10001, staphylococcus; 724, 726, 727, 728, 729, 731, 739, 788, 791, 881, infertility (prevention); 1839, 1999, 2001, 2007, 2009, 2126, 2128, 2129, 4999, 9999, gastospasm; 19, 21, 59, 71, 96, 126, 665, 726, 739, 788, 791, 881, 9999, 10001, calculus of kidney and gallbladder; 665, 728, 791, 801, 881, 9999, 10001, streptococcus; 667, 728, 739, 788, 791, 874, 876, 879, 881, 884, 886, paroxysm, apoplexy, cerebral apoplexy; 19, 21, 61, 71, 94, 126, 788, 791, 879, 4999, 9999, 10001, hordeolum; 19, 21, 61, 71, 94, 126, 788, 791, 879, 4999, 5001, 9999, 10001, sunstroke; 19, 21, 61, 71, 94, 126, 9999, 10001, adrenal stimulation; 19, 21, 61, 71, 94, 126, 4999, 5001, surgery; 665, 726, 728, 741, 786, 788, 791, 879, 881, 5001, tumor (under malleolus); 19, 21, 59, 71, 96, 126, 665, 726, 739, 788, 791, 881, 4999, 9999, 10001, syndrome (in general); 19, 21, 59, 71, 96, 126, 665, 726, 739, 788, 791, 881, 9999, 10001, syphilis; 19, 21, 61, 73, 96, 124, 599, 601, 624, 626, 667, 699, 701, 728, 741, 788, 791, 881, 9999, gustatory anesthesia; 19, 21, 61, 73, 96, 126, 9999, 10001, tetanus; 599, 601, 661, 667, 701, 728, 741, 788, 791, 881, thalamus (part of diencephalon); 19, 21, 61, 71, 94, 126, 4999, 5001, thrombophlebitis; 1499, 1501, 1551, 1601, thrombosis; 19, 21, 61, 71, 96, 126, 791, 799, 801, 1499, 1501, 4999, 5001, thrush; 665, 728, 741, 788, 791, 881, thymus (in general); 19, 21, 59, 71, 94, 126, 667, 728, 741, 788, 791, 881, 4999, 5001, thyroid gland; 19, 59, 71, 96, 124, 159, 161, stimulation of tissue cells; 665, 726, 739, 788, 791, 881, 1841, 1999, 2001, 2999, 3001, 4999, 5001, tonsillitis; 19, 21, 61, 73, 96, 126, 667, 728, 741, 788, 799, 801, 881, 5001, toothache; 19, 21, 667, 728, 741, 788, 791, 881, 4999, poison reaction; 19, 61, 73, 96, 124, trachoma (inflammation of eyes); 726, 788, 881, mental trauma; 665, 728, 741, 786, 791, 881, 5001, 9999, 10001, tuberculosis; 19, 21, 61, 71, 94, 126, 667, 728, 741, 788, 791, 799, 801, 1499, 1501, 1549, 1551, 1599, 1601, tumor in general; 1841, 1997, 1999, 2007, 2009, 2126, 2128, 2129, typhoid; 19, 21, 61, 73, 96, 126, 667, 689, 691, 1499, 1501, 1551, 1569, 1571, 1601, ulcer; 726, 777, 788, 881, unconsciousness, stun; 19, 21, 801, 5001, inflammation in urethra in general; 667, 728, 741, 788, 791, 879, 881, urtication; 1841, 1999, 2001, 2007, 2009, virus disease; 777, 788, 801, 831, 839, 881, 1571, 1999, 2051, 2488, 2491, 4999, verruca; 667, 728, 786, 788, 1841, 1999, 2001, 2007, 2009, 2126, 2128, 2129, whiplash; 19, 21, 61, 73, 96, 126, 9999, 10001, yellow fever; 19, 21, 61, 73, 96, 879, 881, 9999, 10001.

Abscess, tumor, stomachache, acidosis, pimple, actinomycosis, megalgia, adenoids, adhesion, acquired immunodeficiency syndrome, alcoholism, allergy, alopecia (hair loss), amenorrhea (unsuccessful memses), anemia, aneurysm, anus (pruritus ani), spleen ulceration, anthrax (infectious disease of cattle), disinfection, sterilization, appendicitis, cecitis, anorexia, AIDS-related syndrome, arterial sclerosis, artery (stimulate), arteriosclerosis, arthritis, ataxia (muscle), athlete's foot, asthma, star-shaped cerebral or spinal cells, autointoxication, rod virus, backache, respiratory insufficiency, irritability (irritable), fire blister, water blister, water blister, bulla, blood disease, hypotension, tumor, eruption, tumor (rash, contagion), bone (crack, fracture), tumor of breast, region of chest, respiration, Bright's disease (most dangerous nephritis), nephritis, pneumonia, bronchitis, bruise, cut, contusion, bubonic plague, contagious disease, pain of hallux valgus, burn (radiant heat), burn (heat), bursitis, butterfly-shaped erythematous lupus, cancer (sarcoma), cancer (generally, for prevention), cancer (inside, outside), cancer (leukemia), noma, mycosis fungoides, cavernous hemangioma, cutaneous disease of fish, pimple, eruption, cancer, heart disease (sedative effect), cataract, catarrh (inflammation of nasal mucous membrane), cerebral infantile paralysis, cerebrospinal meningitis, gland of neck (wen, swelling), cervicitis, chicken pox, chilblains, frostbite, psychomatic disorder, poor circulation (foot), poor circulation (hand), cold, cough, cold (head), stomachache, colitis (mucosa of colon), conjunctivitis (expansion of eyelid), constipation, contraction of swelling, oozing of pus, spasm, convulsion, corn, coryza, costalgia, convulsion, leg cramp, cut (speed remedy), cystitis, dandruff, deafness, discouragement, melancholy, detoxification, diabetes, diarrhea (dysentery), digestive power, diphtheria, swelled organ, swelled stomach, vertigo, edema, medicinal poisoning, duodenal ulcer, dysmenorrhea (menorrhalgia), indigestion, dyspepsia, colon bacillus, ear, eczema, pulmonary edema, expanded gland, nocturnal enuresis, epididymitis, epididymitis, epilepsy, EB virus, erysipelas (cutaneous inflammation), gullet, auditory tube, nose, ear, eyestrain, eye (whole), facial paralysis, facial spasm, fainting, swoon, fascia, muscle sheath, fatigue, fever (in general), crack of rectum, fistulation, fistula (rectum ulcer), gas in the stomach and intestines, influenza, sitotoxism, foot (ordinary injury), frostbite, gallstone, gallbladder, gangrene, gastritis, all glands, glaucoma, goiter, genital gland (inflammation), gonorrhea, gout, gravel (deposits in urine), gingival inflammation, damaged hair, hallucination, hangover, hay fever, head (oppression), headache, heart (in general), hemorrhage, hemorrhoid, hepatitis (inflammation of liver), hernia of an intervertebral disk, hernia, herpes (zoster blister), hiccough, pain of hip, urticaria, hoarse voice, dizziness in menopause, edema, gastric hyperacidity, hypertension, hypochondriasis (melancholia), dyspnea, hypoxia, inflammation of colon, asthenia, inertia, gigantism, indigestion, dyspepsia, infantile paralysis, contagious disease, inflammation of breast, influenza, influenza, injury, sting of an insect, insomnia, intelligence, intellectuality (for improvement), intercostal neuralgia, intestines (inflammation), intestines (spasm), intestines (in general), drunkenness, excitation, irritable, quick temper, urtication of anus, jaundice, joint (inflammation in general), kidney (general), pain in knee, promotion of secretion of breast milk, languidness, fatigue, weakness, chronic diarrhea, Hansen's disease, leukocyte, leukemia and cancer, abnormal secretion of white discharge from the vagina, whole liver, motor ataxia, lumbago, crooked waist vertebra, lupus, whole lymphatic tissue, malaria, measles, depression, memory, Meniere's disease, meningitis, meningoencephalitis, missed period, menorrhalgia, mental retardation, migraine, Down's syndrome, stomatitis, disease of evacuation, multiple sclerosis, epidemic parotiditis, muscles (restoration), muscular dystrophy, nausea, vomiturition, whole neck, nephritis, dental neuritis, erethism (sedative effect), neuralgia, nervous prostration (fatigue), neuritis, neurosis, nicotinism, nasal disorder, adiposis, occipital neuralgia, testitis, arthritis, osteomyelitis, whole ovary, pain, ache, Parkinson's disease, pancreas, parasite, parathyroid, whole pelvis, pericarditis, periodontal disease, tonic disease, laryngitis, hemorrhoids, threadworm, parasite, placenta (afterbirth), blood plasma, lymphoid plasma (cleaning), pleurisy, (pleura), poison (drug), botulism, ptomaine toxication, narcotic, acute anterior poliomyelitis, polyp (nasal polyp), prostatitis, psoriasis, blepharoptosis, pyorrhea, rabies, hydrophobia, rheumatism, rheumatism and arthritis, nasal catarrh, rachitis, tinea, ringworm, sarcoma, scarlet fever, sciatic neuralgia, scorbutus, paralysis, hemiplegia, zoster, sinus fistula, sinusitis, cutis (hemorrhage), sleeping sickness, dislocation of an intervertebral disk, variola, smallpox, smell (lack, deficiency), diseased smell, sneeze, laryngitis, muscular spasm, unconscious spermatorrhea, spleen (hypertrophy), spondylitis, sprain, wrick in general, dysphemia, staphylococcus, infertility (prevention), gastospasm, calculus of kidney and gallbladder, streptococcus, paroxysm, apoplexy, cerebral apoplexy, hordeolum, sunstroke, adrenal stimulation, surgery, tumor (under malleolus), syndrome (in general), syphilis, gustatory anesthesia, tetanus, thalamus (part of diencephalon), thrombophlebitis, thrombosis, thrush, thymus (in general), thyroid gland, stimulation of tissue cells, tonsillitis, toothache, poison reaction, trachoma (inflammation of eyes, mental trauma, tuberculosis, tumor in general, typhoid, ulcer, unconsciousness, stun, inflammation in urethra in general, urtication, virus disease, verruca, whiplash, and yellow fever.

The selection signal outputting section 24, when an operator inputs an instruction signal through the manual input section 30 according to the kind of disease of interest, for example, No.001 for abscess or tumor, No.002 for stomachache, No.004 for pimple, etc., reads plural frequency data appropriate for the kind of disease from the memory section 22 and outputs them.

Incidentally, with this low-frequency therapeutic apparatus 10, electricity applied to the therapeutic and inactive electrodes 14 and 16 has a maximum voltage of 30 V and a maximum current of 50 mA, and they are below the voltage and current limits over which damages of the human body (or of cells) will result.

The duration of current application is determined for example as three minutes for each frequency, and principally no interruption is necessary at each switching from one frequency to another, but such an interruption may be inserted as appropriate. Further, the duration of three minutes may be somewhat lengthened or contracted.

For treatment, for example, of abscess or tumor, the therapeutic electrode 14 is put on the affected part and the inactive electrode 16 is put at the opposite side to the therapeutic electrode 14 and electric current is made to flow through the affected part placed between them. In case of stomachache, the therapeutic electrode 14 and the inactive electrode 16 are adhered on the skin of the front and back sides of the stomach or intestines so that the two electrodes sandwich the affected organ and current is made to flow through the affected organ between them.

Figure 3:
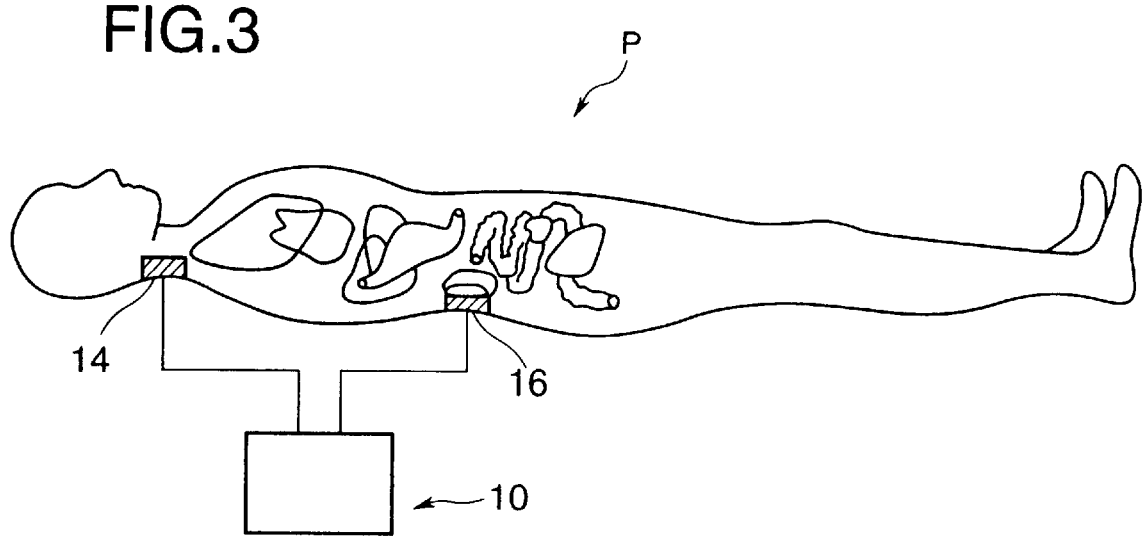
FIG. 3 is a side view showing how treatment proceeds with the same wave therapeutic apparatus.

Some kinds of diseases are often caused by a distorted spinal column, or abnormal disposition or imbalance of muscles being at both sides of the spinal column. For treatment of such a disease, as shown in FIG. 3, the electrodes 14 and 16 are applied one on the posterior surface of the neck of the patient P and the other on the posterior surface of the upper sacrum, and an electric current is passed through between the two electrodes.

Figure 4:
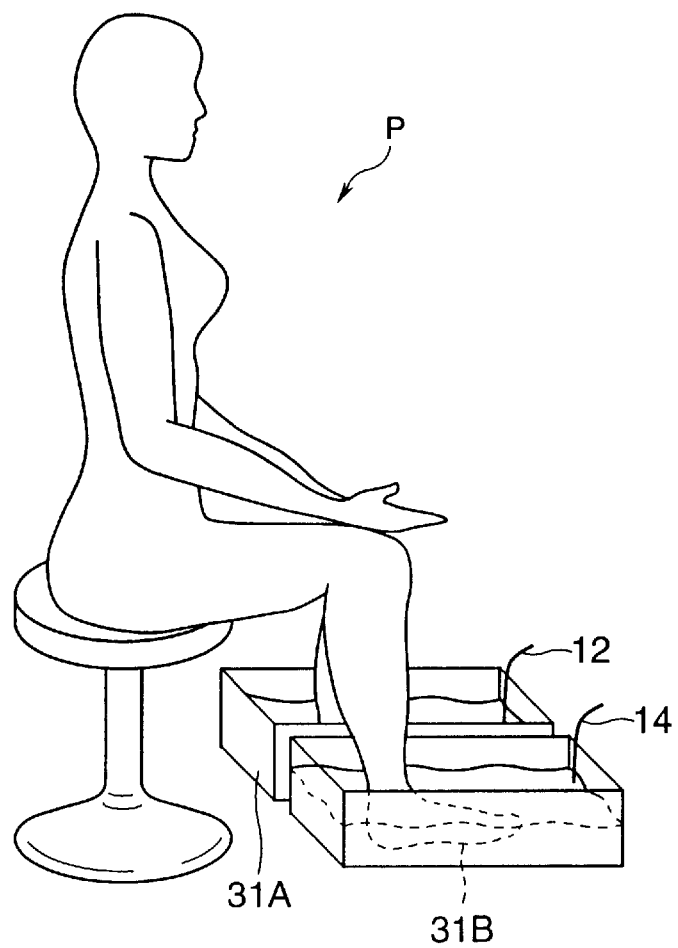
FIG. 4 is a perspective view showing how treatment proceeds with the same wave therapeutic apparatus.

As still another application, for treatment of a lesion located anywhere from the toe to the part just beneath the naval, as shown in FIG. 4, therapy consists of pouring lukewarm water into two basins 31A and 31B, dissolving a small amount-of electrolytes such as table salt in the two volumes of water to reduce the electric resistance thereof having the patient P put his/her feet (from the toe to the heel) one for each basin, placing the therapeutic and inactive electrodes 14 and 16 separately for each basin, and passing an electric current between the two electrodes. For the treatment of a patient having a systemic or chronic disease, the therapy consists of having the patient put his/her feet together in one basin, inserting one electrode into the same basin and placing the other electrode on the neck, and passing a large amount of electrons through the body.

Figure 5:
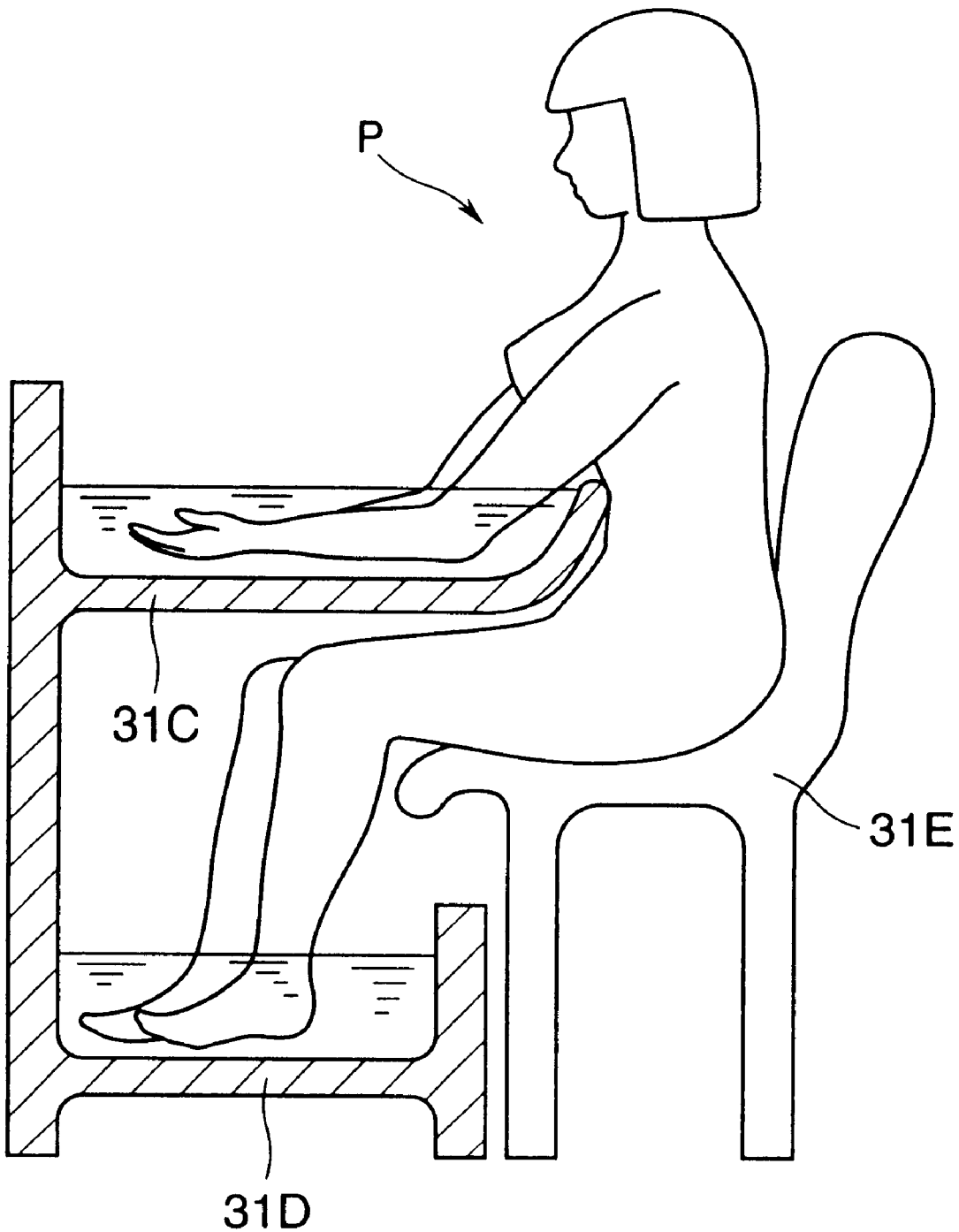
FIG. 5 is a diagrammatic side view showing another example of treatment with the same wave therapeutic apparatus.

An alternative therapy may consist of having the patient put both his/her hands and feet in two basins 31C and 31D separately as shown in FIG. 5, pouring lukewarm water dissolving table salt into the two volumes of water placing the therapeutic and inactive electrodes 14 and 16 separately in the two basins 31C and 31D, and passing an electric current between the two electrodes in the same manner as shown in FIG. 4. In this case, the patient P is allowed to sit on a chair 31E during therapy.

The present inventors found that, prior to the therapy specific for a disease of interest, introduction of a basic therapy which contributes to shift the pH of body fluid of the patient which has been displaced towards acidity, to weak alkalinity will bring about a great therapeutic effect.

Figure 6:
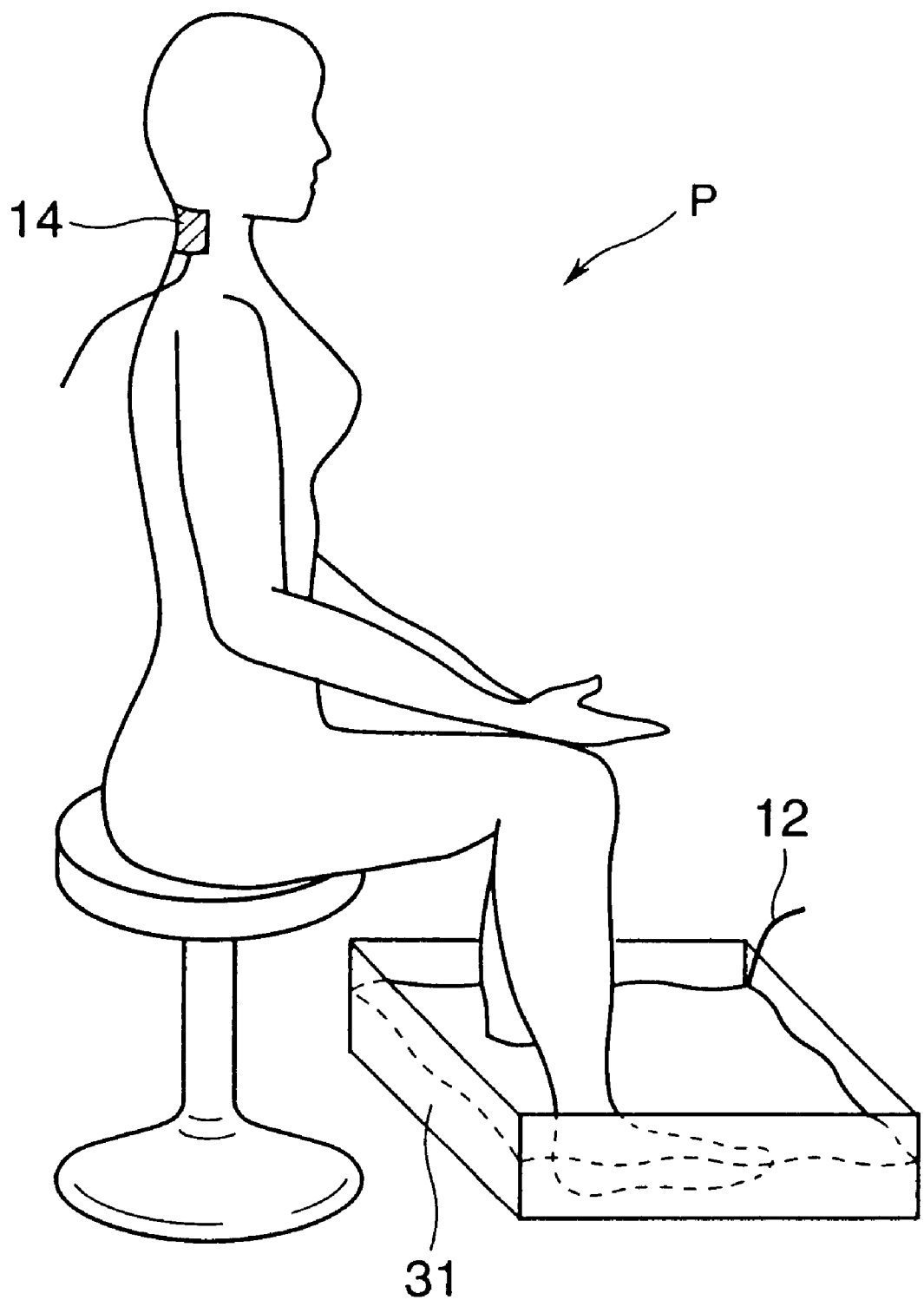
FIG. 6 is a perspective view showing how a basic therapy is performed.

The basic therapy, as shown in FIG. 6, consists of placing one of the therapeutic and inactive electrodes 14 and 16 into a basin 31, having the patient P put his/her bilateral feet into the same basin 31, applying the other electrode on the posterior part of the patient's neck, and passing an electric current between the two electrodes. The basin 31 is filled with lukewarm water dissolving table salt or the like.

The frequency of electric current includes 19, 61, 96, 124, 667, 726, 741, 786, 791, 879 and 10001 Hz, and these frequencies are applied across the two electrodes in this order.

On completion of this basic therapy, the therapy (adaptive therapy) consisting of passage of an electric current having frequencies appropriate for the disease sustained by the patient is undertaken.

In this case, the used frequencies may be totally or partly the same as those of basic therapy or may be totally different from the latter. In addition, the sites of the patient P for application of electrodes 14 and 16 for the adaptive therapy may be the same as or different from those for the basic therapy.

According to clinical experience, for example in the treatment of deafness, the therapy consists of passing an electric current between the two ears, and the patient receiving the therapy came to perceive high frequency sounds considerably well which have been practically inaccessible to perception heretofore. Further, when an electric current was passed between the bilateral temples, the patient came to have an improved vision.

In addition to abscess, stomachache, pimple and the like described above, the therapy was also effective for the treatment of 325 different diseases including, to mention a few, asthma, anemia, arthritis, appendicitis/inflamed cecum/pneumonia, hypotension, burn, nephritis, hypertension, constipation, cystitis, cancer, etc.

However, the definitive reason why the therapy consisting of raising the frequencies of electric current step by step in an ascending order is effective for the treatment of those diseases as described above cannot be offered yet.

Only the following assumption may be presented.

Firstly, each cell has many ionic channels on its cell membrane, but when it has its cell membrane sclerosed, these ionic channels become closed making it impossible to interchange ions such as calcium ions, sodium ions, potassium ions, etc. between the intracelluar and extracelluar spaces, or reducing such interchange to an extremely marginal level. In this state, the patient may be often afflicted with a so-called ionic-channel failure disease. Sclerosis of cell membrane may be result from the injurious effect due for example to oxygen radicals.

And theoretically a minimum of 6 or a maximum of 100 or more water molecules in various body fluids of a human body are linked with one another to form a so-called cluster, and when the number of electrons (minus ions) in the body fluids comes to reduce, the cluster becomes larger.

When a cluster of water molecules is so large as this, even if the ion channels of a cell membrane described above are normal, the cluster of water molecules cannot pass through the cell membrane and brings the same result as said ion channel disease.

In fact also, it has been reported that a cluster of intracelluar fluid of an oncocyte of a human body is larger than that of a normal cell.

As another possible cause, a biochemical phenomenon or a so-called calcium paradox may be mentioned. When the calcium concentration in blood lowers for some reason, calcium constituting bones dissolves into blood, and the dissolved calcium in blood is pushed into the interior of cells through the action of hormones, and the involved cells are exposed to a so-called calcium toxin and become sclerotic. Although calcium is one of minerals essential for vital activity, calcium excessively dissolved in blood is rather harmful to a living body.

As a third possible cause, the following may be mentioned. With respect to muscle cells, calcium enters into the cell interior to act as a trigger for contraction, but when muscle cells generate lactic acid after a hard exercise, calcium binds to the lactic acid to form calcium lactate, which may cause the involved muscle cells to harden.

As a further postulate, the inner wall of an artery is constituted by smooth muscle cells, and when calcium binds to those smooth muscle cells, the involved cells become so sclerotic that they cannot maintain the elasticity of the artery. To compensate for this defect, a new growth of smooth muscle cells occurs over the hardened cells, and such processes are repeated one after another to gradually narrow the cross-sectional area of the artery. This is a known cause for the development of so-called arteriosclerosis.

Even such sclerotic cells, when being exposed to an electric current, naturally contract. When the stimulating current occurs as an alternating current, the involved cells may repeat contraction and relaxation. During the stimulation, however, sclerotic cells do not respond uniformly to all frequencies of stimulating current but contract in response to certain specific frequencies.

Generally, more seriously hardened cells become more responsive to lower frequencies, because they have lost more severely their elasticity. For example, when a hardened cell is exposed to a current having a frequency of 21 Hz, it vibrates just as it is put in resonance with the stimulation, and through the vibration, the sclerotic membrane of the cell is relaxed and resumes a certain degree of elasticity. Accordingly, the cell which has resumed a certain degree of elasticity after being stimulated for example with a current of 21 Hz in frequency becomes responsive or resonant to a current of somewhat higher frequency, say, 61 Hz.

In this manner, raising the frequencies of stimulating current step by step in an ascending order will also raise the resonant frequency of a sclerotic cell, and repeating this therapy will finally lead to the complete recovery of the elasticity inherent to the membrane of the cell. Then, the various ionic channels will become possible to open again, and normal cell activities will become possible which will lead to the healing of the disease.

And it is conceivable also that when an electric current is passed through a large cluster of water molecules as described above, the cluster is made so small that it can pass through the ion channels of a cell membrane and the cell become normal.

Furthermore, application of a current with specific frequencies does not give any harmful effects on the various cells of a human body and their DNA, or rather it is thought beneficial because it may contribute to destruction of viruses and bacteria invading the human body.

To put it more in detail, viruses and bacteria are surrounded by cluster goblets (colloidal membranes) while tissue cells and blood cells of the human body are devoid of such cluster goblets. Thus application of a current having the frequencies specifically destructive to such cluster goblets may destroy viruses and bacteria selectively without inflicting any damage to the host cells. Or, viruses and bacteria whose cluster goblets have been destroyed after exposure to the current having the frequencies specifically destructive to them will lose a capability to regenerate or migrate, so that they cannot develop a resistance to drugs even if they escape destruction brought about by the electric stimulation.

Moreover, an effect that stimulation with an electric current having frequencies of 659, 661, 739, 741, 891, 1839, 1841, 1997, 1999, 4999, 5001, 999 and 10001 Hz relaxes a human body and gives a good sensation, promotes the secretion of a hormone called oxytocin, increases alpha-wave components in EEG, relieves pain associated with disease, and excites human vigor and rejuvenates the activity of cells is also conceivable.

The present inventors found that it is greatly beneficial to have the patient take an aqueous solution of baking soda (sodium bicarbonate) 12 to 24 hours before he/she receives the therapy with the low-frequency therapeutic apparatus 10 of this invention. This is probably because calcium removed from cell membranes during therapy binds to the carbonate group of sodium bicarbonate to form calcium carbonate, which is then excreted.

For therapy, it is effective to apply a therapeutic session successively at five times at intervals of 72 hours at an average, and for treatment of the patient seriously ill or weakened by a chronic disease, it is preferable to employ as the first therapy a session consisting of frequencies not exceeding 1000 Hz.

The frequencies to be used for the therapy with the low-frequency therapeutic apparatus are in the range of 14 to 10001 Hz, and the reason is as follows.

First, with a conventional low-frequency therapeutic apparatus, for stimulation of degenerate nerves and muscles, passage of electric currents at a rate of, for example, one time in a few seconds is required, and the waveform of the electric current must have a long duration. An apparatus of this type is not for stimulating individual cells but is for stimulating a mass of cells representing a muscle. For stimulating individual muscles, it is thought necessary to resort to frequencies not less than 14 Hz.

Setting the upper limit of frequency at 10001 Hz or less was derived from the fact that frequencies exceeding that limit are problematic from the viewpoint of safety to the human body, and that a current of 10001 Hz in frequency greatly relaxes the human body as described earlier.

According to our experiments, it was found that when a session consists of delivering a series of frequencies step by step in an ascending order and the highest frequency is 5001 Hz or 10001 Hz, the therapeutic effect could be enhanced by using 5999 and 5001 Hz or 9999 and 10001 Hz.

And in treatment of arterial aneurysm for example, using 19 and 21 Hz as the lowest frequencies, and 4999 and 5001 Hz as the highest frequencies could also enhance the therapeutic effect.

Figure 7:
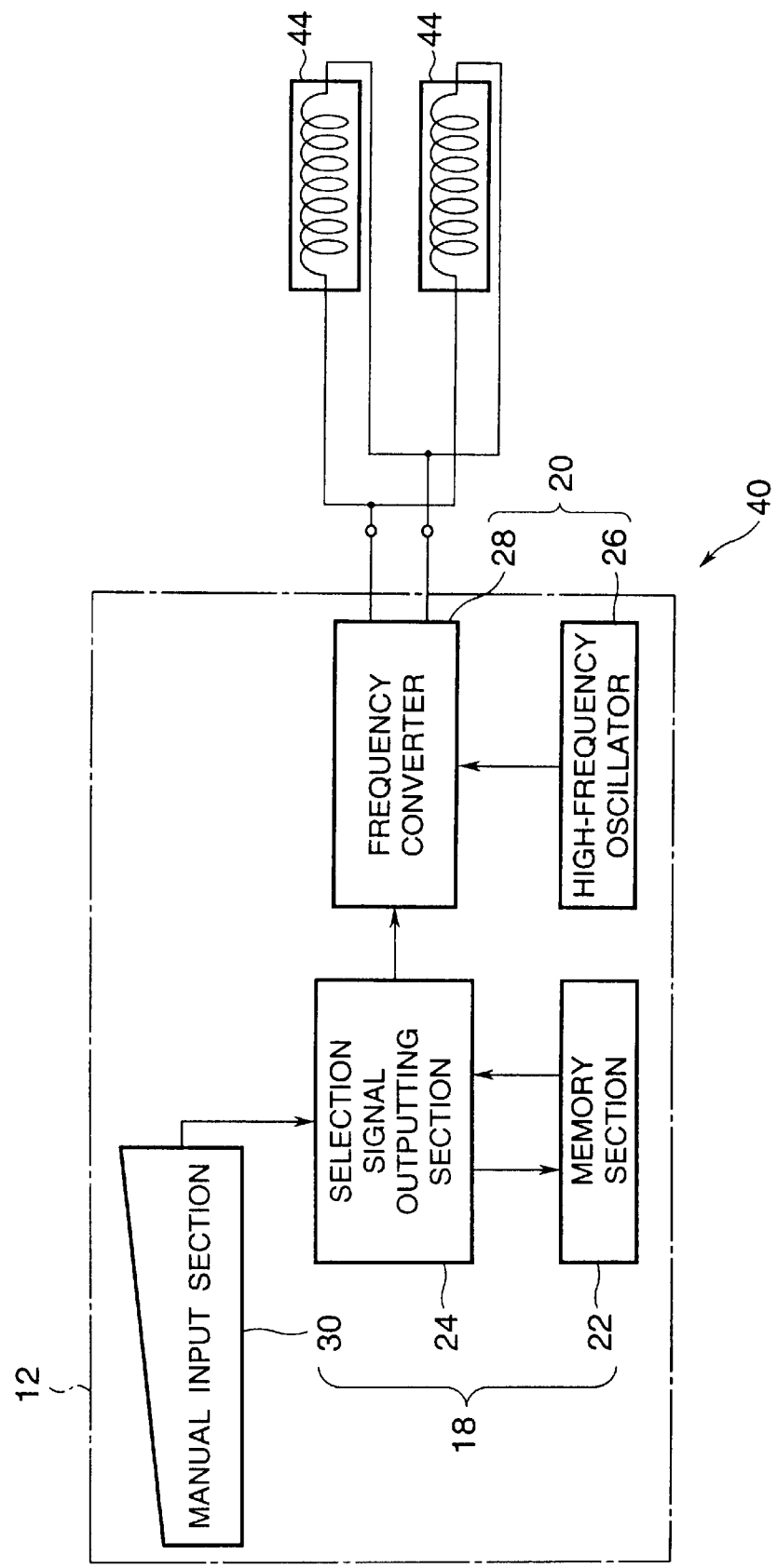
FIG. 7 is a block diagram showing a wave therapeutic apparatus according to a second embodiment of the present invention.
Figure 8:
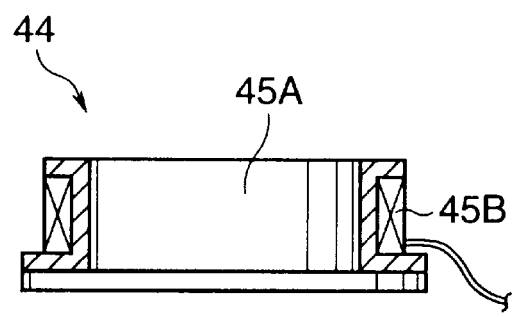
FIG. 8 is a magnified sectional view showing an oscillating coil in the same wave therapeutic apparatus.

As shown in FIG. 7, a wave therapeutic apparatus 40 according to a second embodiment of the present invention is provided with the same oscillator 12 for generating a low-power and low-frequency current as that of the wave therapeutic apparatus 1 of FIG. 1 and a plurality of oscillating coils 42 to be given an electric current outputted from this oscillator 12.

The oscillating coils 42 are arranged closely to a site to be treated of a human body, and as shown in FIG. 2, each of the oscillating coils 42 is formed by winding a coil 15B around a flat iron core 45A and as shown in FIG. 3 for example, when a patient P on a bed 46 lies face up, they are arranged in the vicinity of both sides of his/her spinal column, posterior region of neck, lumber region or the like.

And each of the oscillating coils 42 is set on the bed 46 so that the axis line of its iron core is perpendicular to the upper face of the bed 46.

In this case, the oscillating coil 42 may be buried in a bed pad, mat or the like so that its top does not project and may be covered with a sheet.

Since the oscillator 12 is the same as the first embodiment, description of it is omitted.

In this low-frequency therapeutic apparatus 40, the output of the oscillating section 20 is made to have a maximum voltage of 30 V and a maximum current of 50 mA on a site of human cuticle in an electromagnetic field generated by the oscillating coils 42. These are below the voltage and current limits over which damages of the human body (or of cells) will result.

The duration of current application is also the same as said wave therapeutic apparatus 10.

Figure 9:
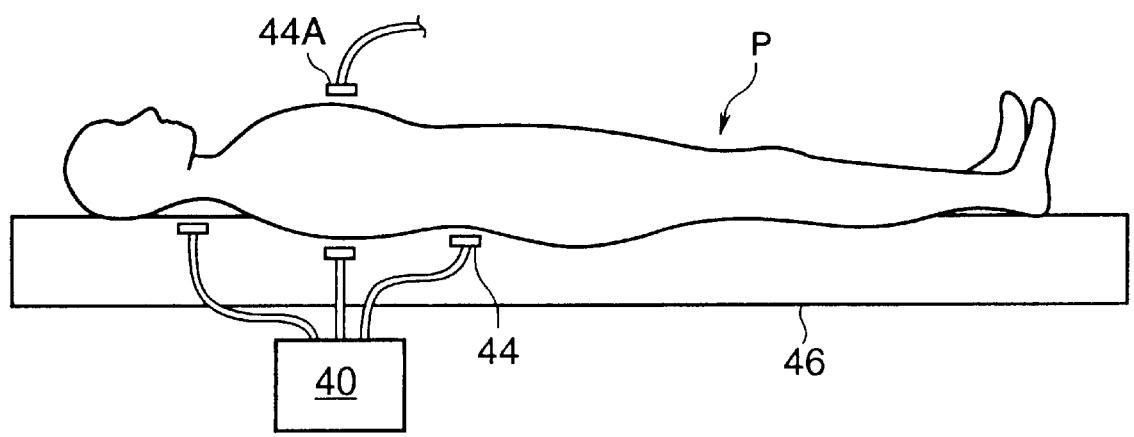
FIG. 9 is a side view showing the arrangement of the coils in the same wave therapeutic apparatus.

Some kinds of diseases are often caused by a distorted spinal column, or abnormal disposition or imbalance of muscles placed on both sides of the spinal column. For treatment of such a disease, as shown in FIG. 9, the oscillating coils 42 are placed one on the posterior surface of the neck of the patient P and the other on the posterior surface of the upper sacrum, and an electromagnetic wave is generated.

Although the patient P may be with his/her clothes on, metal articles such as a watch, belt and the like should be detached. And in case that a pacemaker is in use, it is enough that the pacemaker is electromagnetically shielded with an electromagnetic-shielding sheet placed around it.

For treatment, for example, of abscess or tumor, an oscillating coil 42 on the bed 46 is placed at the back side of the patient and another independent oscillating coil 42 is placed at the opposite side (belly side) so that the affected part is put between the two coils (see FIG. 9) and an electromagnetic field is generated. In case of stomachache, an oscillating coil 44A is placed at the front side of stomach or intestines and an oscillating coil 42 is placed at the back side and an electromagnetic field is generated in a state where the affected part is put between the two coils.

As described earlier, prior to the therapy specific for a disease of interest, introduction of a basic therapy which contributes to shift the pH of body fluids of the patient which have been displaced towards acidity, to weak alkalinity will bring about a great therapeutic effect.

Figure 10:
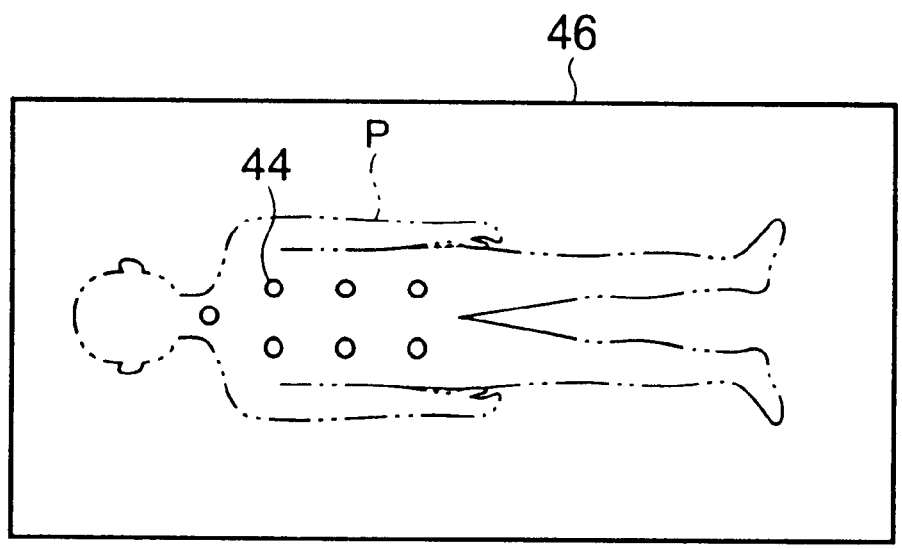
FIG. 10 is a plan view showing how a basic therapy is performed.

The basic therapy, as shown in FIG. 10, consists of exposing the whole back of the patient P to the electromagnetic field of the oscillating coils 42.

After this basic therapy has finished, then the therapy using electromagnetic waves appropriate for the patient's disease is performed.

In this case, the used frequencies may be totally or partly the same as those of the basic therapy or may be totally different from the latter. In addition, the position of the oscillating coil 42 to be attached on the patient P may be the same as or different from the basic therapy.

According to clinical experience, for example in the treatment of hypoacusis, the therapy consists of irradiating the two ears with an electromagnetic wave, and the patient receiving the therapy came to considerably well perceive comparatively high frequency sounds which have been practically inaccessible to perception heretofore. Further, when an electromagnetic wave was irradiated to the bilateral temples, the patient came to have an improved vision.

In addition to abscess, stomachache, pimple and the like described above, the therapy was also effective for many kinds of diseases including asthma, anemia, arthritis, appendicitis/inflamed cecum/pneumonia, hypotension, burn, nephritis, hypertension, constipation, cystitis, cancer, etc.

Figure 11:
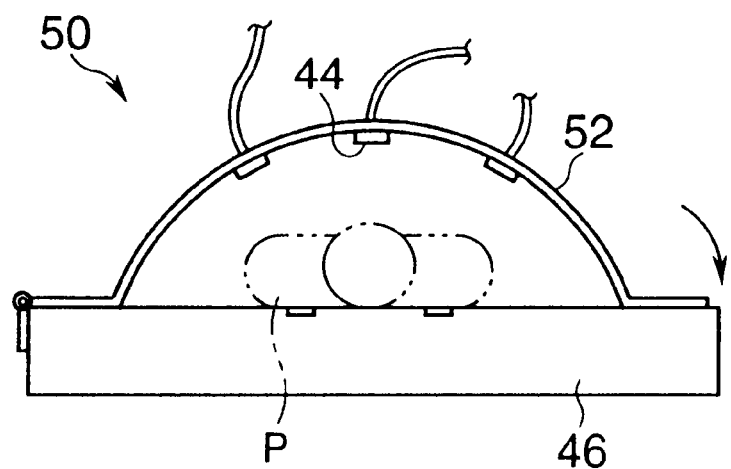
FIG. 11 is a sectional view showing an example of how to use the same wave therapeutic apparatus.

Although the wave therapeutic apparatus 40 according to the above-mentioned embodiment uses an oscillating coil 42 attached to a bed 46 and an oscillating coil 44A capable of being freely placed independently of the oscillating coil 42, the present invention is not limited to this but may adopt an arrangement where like a low-frequency therapeutic apparatus 50 shown in FIG. 11 for example, a cover 52 being freely opened and closed which is made of an electromagnetic-shielding material and is made to cover a bed 46 and a patient P on the bed 46 is provided on the bed 46 and oscillating coils 42 are attached at proper positions on the inner face of this cover 52.

In this wave therapeutic apparatus 50, since the cover 52 is formed out of an electromagnetic-shielding material, the electromagnetic wave outputted from the oscillating coils 42 and 44A does not damage electric appliances around this apparatus by leaking to the outside.

Figure 12:
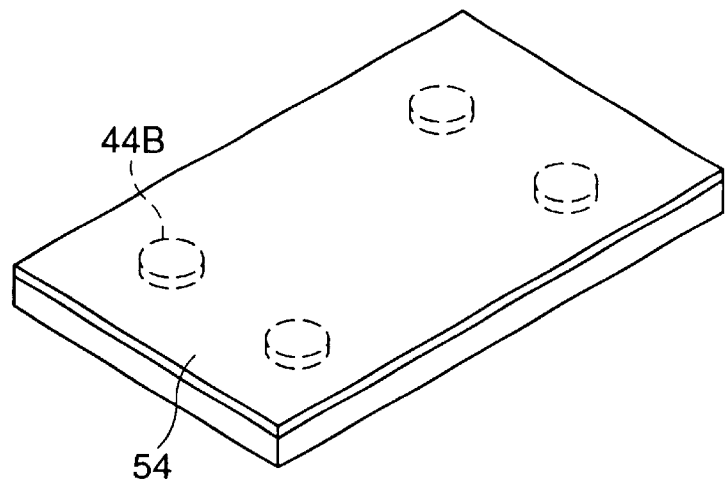
FIG. 12 is a perspective view showing another example of oscillating coils in a wave therapeutic apparatus.

And although said oscillating coils 42 and 44A are separately attached to the bed 46 and the cover 52, a plurality of oscillating coils 44B attached to a flexible supporting member 54 such as synthetic resin, leather, thick cloth or the like may be used, as shown in FIG. 12.

Figure 13:
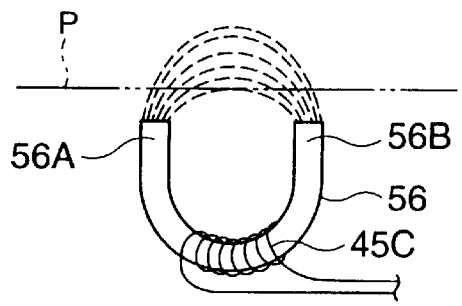
FIG. 13 is a perspective view showing a further other example of the oscillating coils.

Further, although said oscillating coils 44A and 44B each are formed by winding a coil 45B around a flat iron core 45A as described above, the present invention is not limited to this but may adopt an arrangement where as shown in FIG. 13 for example, a coil 45C is wound around a U-shaped iron core 56.

In this case, since an electromagnetic wave is generated between the two top ends 56A and 56B of the U-shaped iron core 56, a patient P is set so that his/her cuticle comes into the electromagnetic field between the top ends 56A and 56B.

Figure 14:
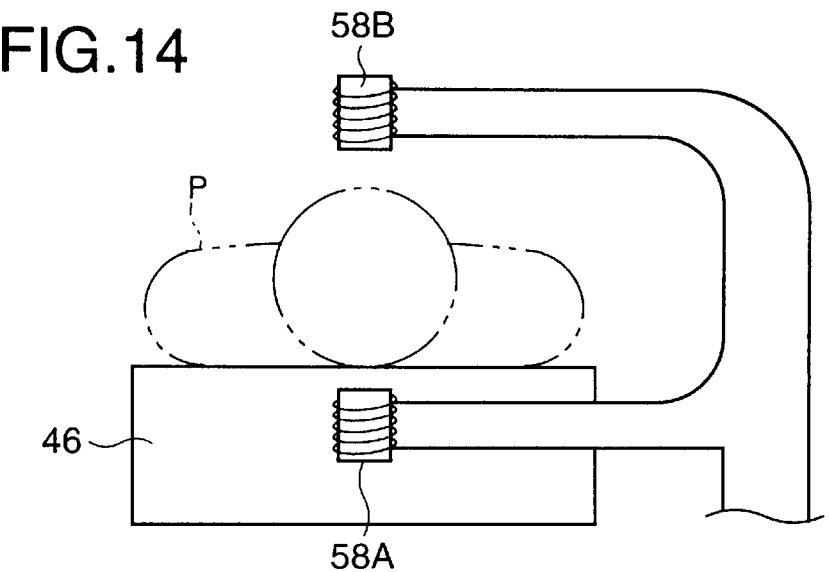
FIG. 14 is a side view showing a still further other example of the oscillating coils.

Furthermore, as shown in FIG. 14, a linear electromagnetic wave may be generated between a pair of coils 58A and 58B by connecting in series the coils 58A and 58B to put the affected part of a patient P between them.

Figure 15:
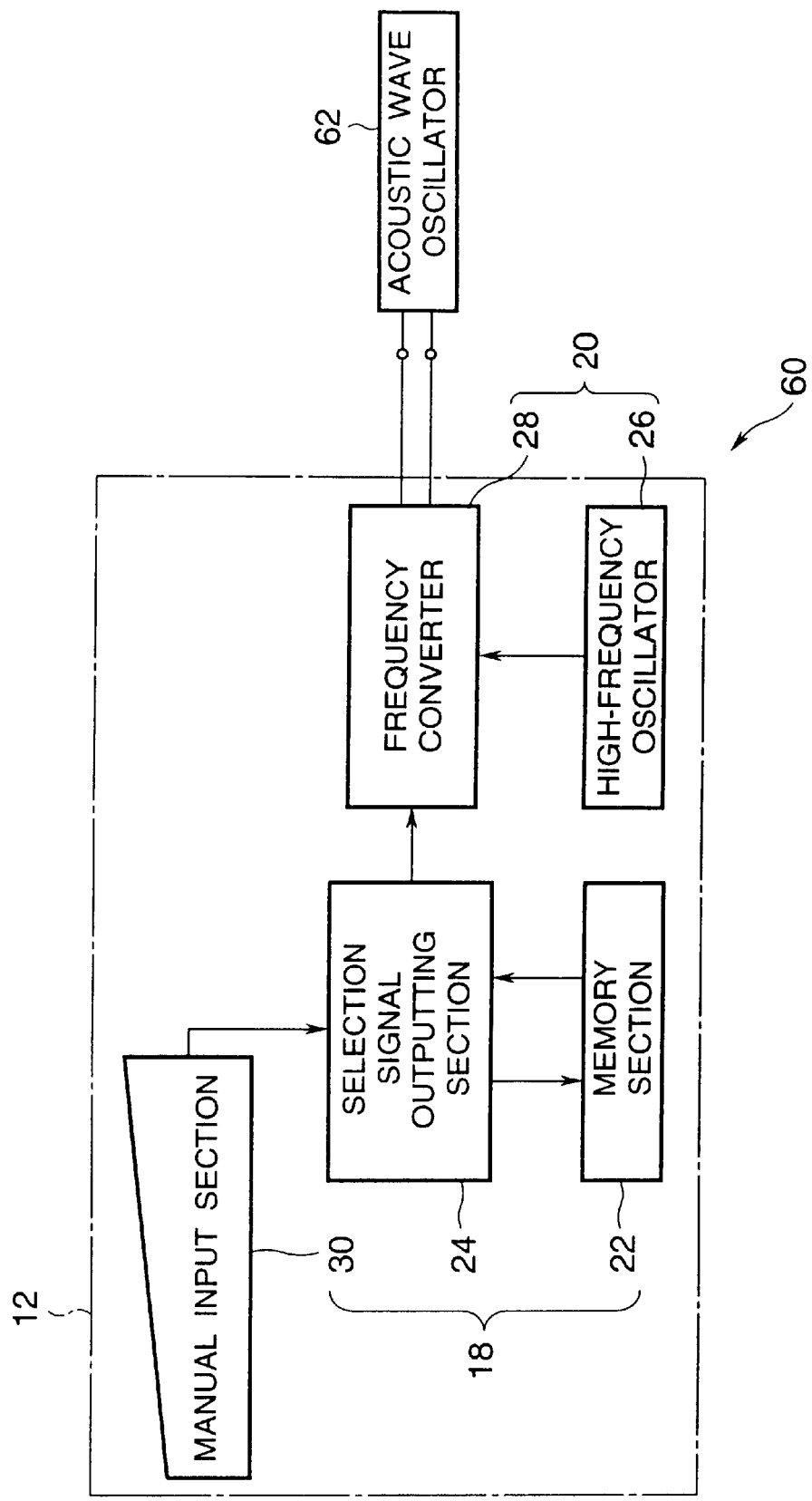
FIG. 15 is a block diagram showing a wave therapeutic apparatus according to a third embodiment of the present invention.

Next, a wave therapeutic apparatus 60 according to a third embodiment of the present invention shown in FIG. 15 is described.

Figure 16:
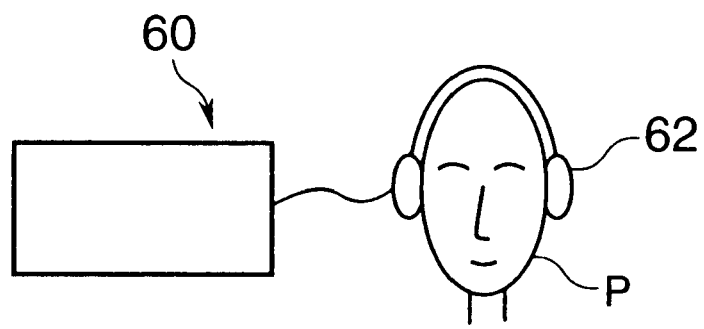
FIG. 16 is a front view showing a state where an acoustic oscillator in the same wave therapeutic apparatus is used.

This wave therapeutic apparatus 60 comprises the same oscillator 12 as that of the wave therapeutic apparatus 10 of FIG. 1 or the wave therapeutic apparatus 40 of FIG. 7, and an acoustic wave oscillator 62 for generating by means of an electric current outputted from this oscillator 12 an acoustic wave having the same frequency as this outputted electric current, and this acoustic oscillator 62 comprises a headphone as shown in FIG. 16 and can pour an acoustic wave of a specific frequency into both ears of a patient P.

Since the oscillator 12 is the same as the first and second embodiments, description of it is omitted.

In this low-frequency therapeutic apparatus 60 also, a plurality of frequency data appropriate for the kind of a disease are read from a memory section 22 and acoustic waves of these frequencies are poured into the ears of the patient P from the acoustic oscillator 62.

In case of pouring an acoustic wave having the same frequency as a low-frequency current in said wave therapeutic apparatus 10 or an electromagnetic wave in said wave therapeutic apparatus 40 in such a way also, the same therapeutic effect as that in said wave therapeutic apparatuses 10 and 40 could be obtained.

Differently from said wave therapeutic apparatuses 10 and 40, this wave therapeutic apparatus 60 is particularly characterized by a fact that it is possible also to obtain a therapeutic effect only by pouring an acoustic wave of a specific frequency into the ears of a patient without putting the affected part between therapeutic devices.

And in case of pouring an acoustic wave of a specific frequency into a patient P, a method called a body sonic method of pouring an acoustic wave directly into a human body through the cuticle of it may be performed.

Figure 17:
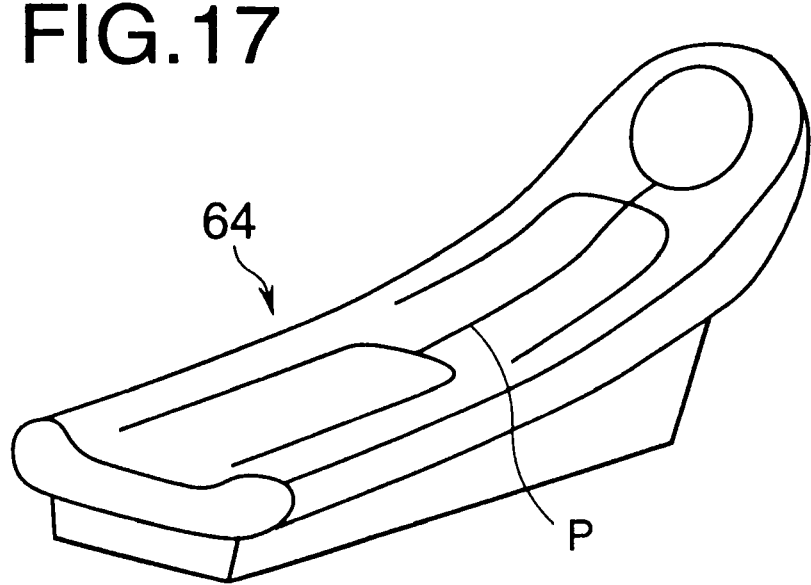
FIG. 17 is a perspective view showing a state where an acoustic oscillator in the same wave therapeutic apparatus is replaced with a body sonic apparatus.

In this case, as shown in FIG. 17, it is preferable to make a patient P lie face up on a body sonic apparatus 64 and pour an acoustic wave into the patient P through his/her back or the like.

It is preferable also to use together the body sonic apparatus 64 and said acoustic wave oscillator 62, and pour acoustic waves having the same frequency as each other into the body of a patient from the body sonic apparatus 64 and into the ears of the patient from the acoustic wave oscillator 62 synchronously with each other.

Figure 18:
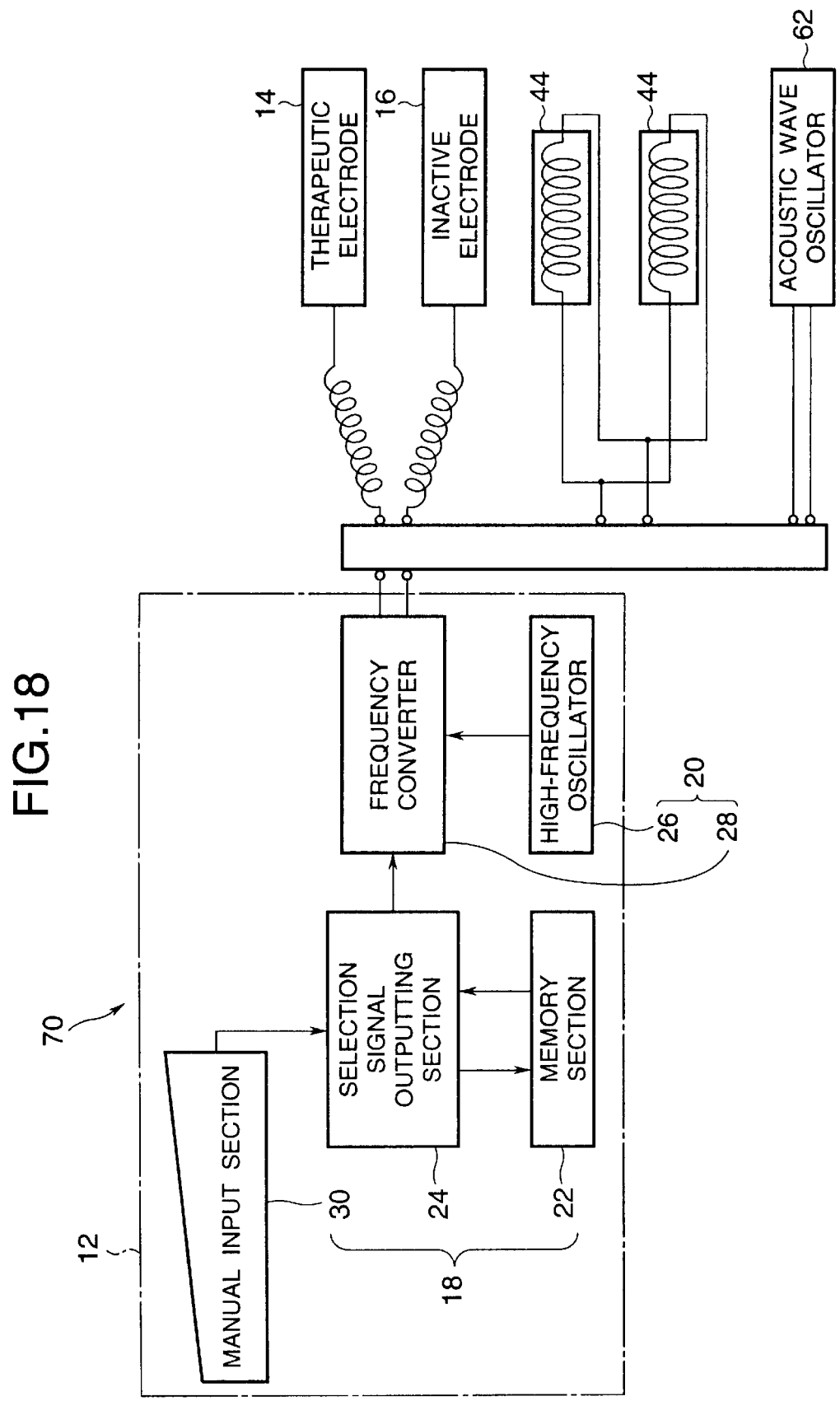
FIG. 18 is a block diagram showing a wave therapeutic apparatus according to a fourth embodiment of the present invention.

Next, a wave therapeutic apparatus 70 according to a fourth embodiment of the present invention shown in FIG. 18 is described.

This wave therapeutic apparatus 70 is provided with an oscillator 12, therapeutic electrodes 14 and 16 as shown in FIG. 1, oscillating coils 44 and/or 44A, and an acoustic oscillator 62 and/or a body sonic apparatus 64, and is made so as to make it possible to inject a low-frequency current directly into the affected part from the therapeutic electrode 14 and the inactive electrode 16, inject an electromagnetic wave into a patient P from the oscillating coils 44 and/or 44A, pour an acoustic wave into the patient P from said acoustic wave oscillator 62 and/or a body sonic apparatus 64, or inject these waves at the same time.

That is to say, this wave therapeutic apparatus 70 is provided with a function obtained by combining with one another a low-frequency electric current applying apparatus, an electromagnetic wave applying apparatus and an acoustic wave applying apparatus, and can perform therapy using these at the same time or separately according to the state of a patient.

For example, it is possible to pour an acoustic wave into a patient P at the same time as when injecting a low-frequency current into the patient P from the therapeutic electrode 14 and the inactive electrode 16.

Figure 19:
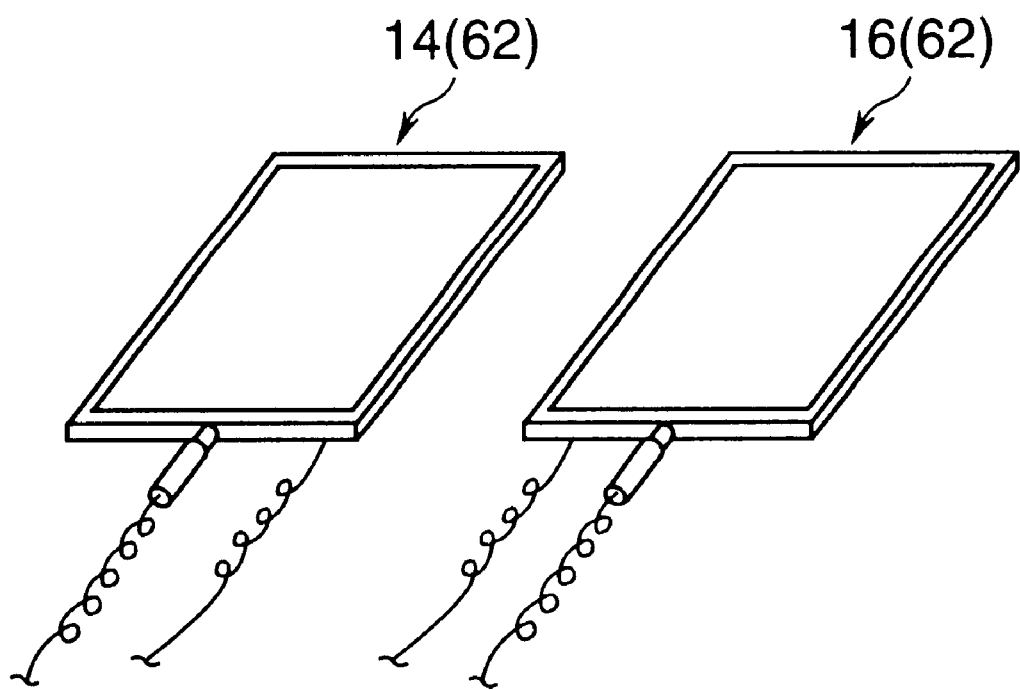
FIG. 19 is a perspective view showing an electrode functioning also as an acoustic oscillator in the same wave therapeutic apparatus according to the fourth embodiment.

In this case, as shown in FIG. 19, if one or both of the therapeutic electrode 14 and the inactive electrode 16 are made to function also as an acoustic wave oscillator, it is possible to perform a more effective therapy.

Next, a wave therapeutic apparatus 80 according to the fourth embodiment of the present invention is described with reference to FIG. 20.

This wave therapeutic apparatus 80, which is controlled through a communication circuit, has an external controller 84, for example, a computer provided remotely from an oscillator 88 as a component equivalent to the frequency controller 18 in the wave therapeutic apparatus 10, 40, 60 or 70 of FIG. 1, 7, 15 or 18, and the frequency and duration of oscillation of it can be controlled by this external controller 84 through a communication circuit 86.

The external controller 84 is composed of a computer and is provided with a memory section 84A, a selection signal outputting section 84B and a manual input section 84C.

And the oscillator 88 is provided with a high-frequency oscillator 88A and a frequency converter 88B, and is made so that its control signal is inputted through an I/O interface 90B from the communication circuit 86.

Said external controller 84 and communication circuit 86 are also connected with each other through an I/O interface 90A.

The actual usage of this wave therapeutic apparatus 80 is as follows.

First, a user (patient or operator) informs an operator (physician or his/her assistant) of the external controller 82 of the name of the patient's disease through the communication circuit 86 and asks for a wave therapy.

In a low-frequency therapy, the operator instructs the user the positions where a therapeutic electrode 14 and an inactive electrode 16 are to be attached to the patient according to the disease name, and then inputs a code number corresponding to the disease name, for example, number 001 in case of arterial sclerosis as described above from the manual input section 84C.

The oscillator 88 at the patient side, which has been activated in advance by the external controller 84 through the telephone circuit 86, reads in order frequencies appropriate for the disease name from the memory section 84A by input to the manual input section 84C and controls the frequency controller 88B in the oscillator 88 at the patient side from the selection signal outputting section 84B.

In this way, the frequencies specified for the disease name are selected one after another in an ascending order at intervals of a specified time and are outputted between the therapeutic electrode 14 and the inactive electrode 16.

After a specific therapy time has passed, the external controller 84 stops the oscillator 88 through the communication circuit 86.

A therapeutic system as described above has an advantage that it is not necessary to update an individual memory section of a wave therapeutic apparatus at the patient side in case that frequencies to be used in a wave therapy of the present invention have been changed or added due to a further study, or in case that a set of frequencies corresponding to a new disease has been determined.

Further, when a patient or his/her attendant asks for a question or gives some information, a physician or an expert operator can always take a proper action, and thereby can prevent the patient or the attendant from being indulged in irrational use of the therapeutic apparatus based solely on his/her dogmatism.

In order to monitor where the therapeutic electrode 14 and the inactive electrode 16 are to be attached and where the oscillating coils 44 and 44A are to be set, and where an acoustic wave is to be applied, image data representing the setting positions of these therapeutic devices corresponding to a disease name may be read from the image memory section 94 at the external controller 84 side and displayed on a display 92 provided in addition to the oscillator 88, as shown by alternate long and two short dashes lines in FIG. 20.

Although the above-mentioned embodiments are related to a therapeutic method and apparatus for a human body, the present invention is not limited to these, but according to experiments of the present inventors, a similar therapeutic effect to that in case of a human being has been able to be obtained by applying waves having said frequencies to a mammal, for example, a domestic animal such as a dog, cat, horse, cattle, pig, etc.

INDUSTRIAL APPLICABILITY

According to this invention, it is possible to bring about an excellent therapeutic effect by relaxing sclerotic cells so as to recover their normal vigor safely without inflicting any adverse effects to a human body, or by annihilating bacteria and viruses as foreign organisms parasitic to a human body, and further by enhancing a living body's immunity.

What is claimed is:

1. A wave therapeutic method for performing treatment by applying to a human body at least one of a low-frequency electric current, electromagnetic wave and acoustic wave, said method performing treatment by selecting as the frequencies of said waves at least two frequencies from among 14, 16, 19, 21, 25, 27, 59, 61, 71, 73, 94, 96, 119, 121, 124, 126, 159, 161, 441, 447, 449, 464, 466, 499, 501, 599, 601, 624, 626, 659, 661, 665, 667, 689, 691, 699, 701, 724, 726, 727, 728, 729, 731, 739, 741, 769, 771, 775, 777, 786, 788, 789, 791, 799, 800, 801, 802, 803, 804, 805, 831, 839, 874, 876, 879, 881, 884, 886, 891, 1499, 1501, 1549, 1551, 1559, 1561, 1569, 1571, 1599, 1601, 1799, 1801, 1839, 1841, 1849, 1851, 1899, 1901, 1997, 1999, 2001, 2007, 2009, 2051, 2099, 2101, 2121, 2126, 2127, 2128, 2129, 2131, 2488, 2489, 2490, 2491, 2999, 3001, 4999, 5001, 9999 and 10001 Hz according to a disease and making the frequencies higher in order at intervals of a specified time.

2. A wave therapeutic method according to claim 1, which method performs treatment by;
first using as a basic therapy waves of 19, 61, 96, 124, 667, 726, 741, 786, 791, 879 and 10001 Hz in frequency in this order, and
next using waves having frequencies selected according to the kind of a disease.

3. A wave therapeutic method according to claim 1 or 2, which method performs treatment by applying each of the waves having said selected frequencies to a human body for 2 to 5 minutes.

4. A wave therapeutic method according to claim 1 or 2, wherein a pause of 0 to 1 minute is provided when said selected frequencies are changed over.

5. A wave therapeutic method according to claim 1 or 2, wherein the lowest frequency of said selected frequencies is set at 14 Hz.

6. A wave therapeutic method according to claim 1 or 2, wherein at least two frequencies of 21, 59, 73, 94, 99, 121, 126, 447, 449, 464, 466, 499, 599, 626, 659, 667, 728, 739, 777, 788, 791, 799, 802, 805, 881, 1499, 1549, 1571, 1601, 1799. 1839, 1999, 2001, 2009, 2128, 2488, 2489, 2490, 2491, 4999 and 9999 Hz are used as said frequencies in case that a disease to be treated is acquired immunodeficiency syndrome.

7. A wave therapeutic method according to claim 1 or 2, wherein at least two frequencies of 667, 726, 741, 786, 791, 879, 4999 and 5001 Hz are used as said frequencies in case that a disease to be treated is allergy.

8. A wave therapeutic method according to claim 1 or 2, wherein at least two frequencies of 21, 61, 71, 96, 124, 665, 728, 741, 788, 791, 881, 4999, 5001, 9999 and 10001 Hz are used as said frequencies in case that a disease to be treated is arteriosclerosis.

9. A wave therapeutic method according to claim 1 or 2, wherein at least two frequencies of 19, 21, 59, 71, 94, 126, 667, 726, 739, 786, 791, 801, 881, 1501, 1841, 1999, 2001, 2007, 2126, 4999, 5001, 9999 and 10001 Hz are used as said frequencies in case that a disease to be treated is arthritis.

10. A wave therapeutic method according to claim 1 or 2, wherein at least two frequencies of 667, 728, 741, 788, 789 and 881 Hz are used as said frequencies in case that a disease to be treated is asthma.

11. A wave therapeutic method according to claim 1 or 2, wherein at least two frequencies of 61, 96, 124, 667, 726, 741, 786, 791, 879 and 10001 Hz are used as said frequencies in case that a disease to be treated is hypotension.

12. A wave therapeutic method according to claim 1 or 2, wherein at least two frequencies of 19, 21, 59, 71, 94, 124, 667, 728, 739, 786, 791 and 879 Hz are used as said frequencies in case that a disease to be treated is tumor, eruption.

13. A wave therapeutic method according to claim 1 or 2, wherein at least two frequencies of 665, 728, 741, 777, 791 and 881 Hz are used as said frequencies in case that a disease to be treated is pneumonia.

14. A wave therapeutic method according to claim 1 or 2, wherein at least two frequencies of 667, 728, 741 and 879 Hz are used as said frequencies in case that a disease to be treated is bronchitis.

15. A wave therapeutic method according to claim 1 or 2, wherein at least two frequencies of 1999, 2001, 2007, 2009, 2126 and 2128 Hz are used as said frequencies in case that a disease to be treated is cancer (sarcoma).

16. A wave therapeutic method according to claim 1 or 2, wherein at least two frequencies of 2121, 2126 and 2131 Hz are used as said frequencies in case that a disease to be treated is cancer.

17. A wave therapeutic method according to claim 1 or 2, wherein at least two frequencies of 667, 726, 741, 788, 791, 879, 4999, 5001, 9999 and 10001 Hz are used as said frequencies in case that a disease to be treated is cataract.

18. A wave therapeutic method according to claim 1 or 2, wherein at least two frequencies of 665, 727, 729, 741, 788, 791, 801, 881, 4999, 5001, 9999 and 10001 Hz are used as said frequencies in case that a disease to be treated is cold, cough.

19. A wave therapeutic method according to claim 1 or 2, wherein at least two frequencies of 19, 61, 73, 96, 124, 667, 728, 739, 788, 789, 791, 799, 801 and 881 Hz are used as said frequencies in case that a disease to be treated is stomachache.

20. A wave therapeutic method according to claim 1 or 2, wherein at least two frequencies of 21, 59, 71, 94, 126, 665, 726, 741, 786, 789, 799, 801, 881, 9999 and 10001 Hz are used as said frequencies in case that a disease to be treated is colitis.

21. A wave therapeutic method according to claim 1 or 2, wherein at least two frequencies of 19, 59, 73, 96, 126, 667, 728, 741, 786, 789, 791, 799, 801 and 881 Hz are used as said frequencies in case that a disease to be treated is constipation.

22. A wave therapeutic method according to claim 1 or 2, wherein at least two frequencies of 21, 61, 71, 94, 126, 665, 739, 788, 791, 799, 801, 881, 4999, 9999 and 10001 Hz are used as said frequencies in case that a disease to be treated is cystitis.

23. A wave therapeutic method according to claim 1 or 2, wherein at least two frequencies of 21, 59, 73, 94, 126, 665, 728, 786, 791, 799, 881, 4999, 9999 and 10001 Hz are used as said frequencies in case that a disease to be treated is diabetes.

24. A wave therapeutic method according to claim 1 or 2, wherein at least two frequencies of 667, 726, 728, 741, 786, 788, 791, 879, 881, 9999 and 10001 Hz are used as said frequencies in case that a disease to be treated is duodenal ulcer.

25. A wave therapeutic method according to claim 1 or 2, wherein at least two frequencies of 665, 726, 728, 741, 786, 788, 789, 879 and 881 Hz are used as aid frequencies in case that a disease to be treated is edema, pulmonary edema.

26. A wave therapeutic method according to claim 1 or 2, wherein at least two frequencies of 19, 61, 71, 94, 124, 667, 728, 741, 786, 791, 799, 801 and 881 Hz are used as said frequencies in case that a disease to be treated is influenza.

27. A wave therapeutic method according to claim 1 or 2, wherein at least two frequencies of 19, 21, 61, 71, 94, 124, 667, 728, 741, 788, 789, 881 and 4999 Hz are used as said frequencies in case that a disease to be treated is gallstone.

28. A wave therapeutic method according to claim 1 or 2, wherein at least two frequencies of 19, 21, 61, 71, 94, 124, 667, 728, 741, 788, 789, 881, 4999 and 5001 Hz are used as said frequencies in case that a disease to be treated is gallbladder.

29. A wave therapeutic method according to claim 1 or 2, wherein at least two frequencies of 19, 21, 61, 71, 94, 124, 667, 728, 741, 788, 789, 881, 4999, 9999 and 10001 Hz are used as said frequencies in case that a disease to be treated is gout.

30. A wave therapeutic method according to claim 1 or 2, wherein at least two frequencies of 19, 21, 59, 71, 96, 126, 667, 728, 741, 789, 799, 801, 879 and 881 Hz are used as said frequencies in case that a disease to be treated is hemorrhoid.

31. A wave therapeutic method according to claim 1 or 2, wherein at least two frequencies of 665, 26, 727, 729, 741, 791, 801, 879 and 881 Hz are used as said frequencies in case that a disease to be treated is hepatitis (inflammation of liver).

32. A wave therapeutic method according to claim 1 or 2, wherein at least two frequencies of 667, 726, 739, 788, 789, 4999 and 5001 Hz are used as said frequencies in case that a disease to be treated is hernia.

33. A wave therapeutic method according to claim 1 or 2, wherein at least two frequencies of 19, 21, 61, 73, 96, 126, 667, 728, 741, 788, 791, 881, 9999 and 10001 Hz are used as said frequencies in case that a disease to be treated is hypertension.

34. A wave therapeutic method according to claim 1 or 2, wherein at least two frequencies of 665, 728, 741, 788, 791, 799, 801, 881, 9999 and 10001 Hz are used as said frequencies in case that a disease to be treated is intercostal neuralgia.

35. A wave therapeutic method according to claim 1 or 2, wherein at least two frequencies of 665, 728, 739, 786, 791, 779, 1999, 2001, 2009, 2126 and 2128 Hz are used as said frequencies in case that a disease to be treated is leukemia and cancer.

36. A wave therapeutic method according to claim 1 or 2, wherein at least two frequencies of 667, 728, 741, 788, 791, 881, 9999 and 10001 Hz are used as aid frequencies in case that a disease to be treated is lumbago.

37. A wave therapeutic method according to claim 1 or 2, wherein at least two frequencies of 19, 21, 61, 71, 96, 126, 667, 728, 741, 788, 791, 879, 881, 4999, 5001, 9999 and 10001 Hz are used as said frequencies in case that a disease to be treated is Meniere's disease.

38. A wave therapeutic method according to claim 1 or 2, wherein at least two frequencies of 19, 21, 61, 73, 96, 126, 667, 728, 741, 788, 791, 799, 881, 9999 and 10001 Hz are used as said frequencies in case that a disease to be treated is nephritis.

39. A wave therapeutic method according to claim 1 or 2, wherein at least two frequencies of 21, 61, 73, 96, 126, 667, 726, 741, 788, 879, 9999 and 10001 Hz are used as said frequencies in case that a disease to be treated is neuralgia.

40. A wave therapeutic method according to claim 1 or 2, wherein at least two frequencies of 667, 726, 741, 791, 879, 1501, 1601, 1839, 1999, 2001, 4999 and 5001 Hz are used as said frequencies in case that a disease to be treated is Parkinson's disease.

41. A wave therapeutic method according to claim 1 or 2, wherein at least two frequencies of 19, 21, 71, 94, 124, 665, 726, 741, 769, 771, 775, 777, 788, 791, 879, 881, 4999 and 5001 Hz are used as said frequencies in case that a disease to be treated is pneumonia.

42. A wave therapeutic method according to claim 1 or 2, wherein at least two frequencies of 19, 59, 71, 94, 124, 599, 659, 667, 728, 739, 788, 791, 801, 881, 1501, 1549, 1601, 1839, 1999, 2001, 2007, 2128, 2129, 4999, 9999 and 10001 Hz are used as said frequencies in case that a disease to be treated is rheumatism and arthritis.

43. A wave therapeutic method according to claim 1 or 2, wherein at least two frequencies of 665, 726, 727, 729, 739, 786, 788, 789, 879 and 881 Hz are used as said frequencies in case that a disease to be treated is laryngitis.

44. A wave therapeutic method according to claim 1 or 2, wherein at least two frequencies of 665, 728, 791, 801, 881, 9999 and 10001 Hz are used as said frequencies in case that a disease to be treated is calculus of kidney and gallbladder.

45. A wave therapeutic method according to claim 1 or 2, wherein at least two frequencies of 19, 21, 61, 73, 96, 126, 667, 728, 741, 788, 799, 801, 881 and 5001 Hz are used as said frequencies in case that a disease to be treated is tonsillitis.

46. A wave therapeutic method according to claim 1 or 2, wherein at least two frequencies of 19, 21, 667, 728, 741, 788, 791, 881 and 4999 Hz are used as said frequencies in case that a disease to be treated is toothache.

47. A wave therapeutic method according to claim 1 or 2, wherein at least two frequencies of 19, 21, 61, 71, 94, 126, 667, 728, 741, 788, 791, 799, 801, 1499, 1501, 1549, 1551, 1599 and 1601 Hz are used as said frequencies in case that a disease to be treated is tuberculosis.

48. A wave therapeutic method according to claim 1 or 2, wherein at least two frequencies of 19, 21, 61, 73, 96, 126, 9999 and 10001 Hz are used as said frequencies in case that a disease to be treated is whiplash.

49. A wave therapeutic method according to one of claim 1 or 2, wherein the frequencies at which electricity is passed through a living body are in a range of said selected frequencies plus or minus 3 Hz.

50. A wave therapeutic method according to one of claim 1 or 2, wherein a low-frequency current is applied between a pair of electrodes brought into contact with the skin so as to put the affected part of a living body between them.

51. A wave therapeutic method according to claim 1 or 2, wherein therapy is performed by arranging at least one oscillating coil of a low-frequency oscillator in the vicinity of a living body and irradiating the living body with an electromagnetic wave having a frequency in a range of at least a part of 14 to 10001 Hz through this coil as making the frequency higher in order at intervals of a specified time.

52. A wave therapeutic method according to claim 51, wherein the strength of an electromagnetic wave generated by said oscillating coil has a maximum of 30 V in voltage and a maximum of 50 mA in current on the cuticle of a human body in the electromagnetic field.

53. A wave therapeutic method according to claim 1 or 2, wherein acoustic waves of said frequencies are poured into a living body from at least one of the ears and the skin of the patient.

54. A wave therapeutic method according to claim 1 or 2, wherein one of said low-frequency electric current and electromagnetic wave, and said acoustic wave which are the same in frequency and synchronous with each other are injected into a living body.

55. A wave therapeutic apparatus (10), (40), (60) or (70) having at least one of a low-frequency electric current applying apparatus (10) which comprises a therapeutic electrode (14) to be put on a site to be treated and an inactive electrode (16) forming a counterpart to this therapeutic electrode (14), being to be put on a living body (P) and serving to pass an electric current through said living body (P) and which applies a low-frequency and low-power electric current wave between these electrodes, an electromagnetic wave applying apparatus (40) which is provided with at least one oscillating coil (44) capable of being placed in the vicinity of a site to be treated of a living body (P), makes the oscillating coil (44) generate an electromagnetic wave by means of a low-frequency current, and applies the electromagnetic wave to the living body (P), and an acoustic wave applying apparatus (60) which pours an acoustic wave generated by an acoustic wave oscillator (62) into at least one of the ears and the skin of a living body (P), wherein;

the frequencies of said waves are generated by an oscillator (12), said oscillator (12) is provided with a frequency controller (18) which selects an oscillation frequency from among a plurality of predetermined frequencies and makes the oscillation frequency higher step by step in an ascending order at intervals of a specified time, said frequency controller (18) has a memory section (22) for memorizing information of a plurality of frequencies selected in advance correspondingly to each of the kinds of diseases and a selection signal outputting section (24) for reading the corresponding information of said plurality of frequencies from said memory section (22) in response to an instruction signal inputted according to the kind of a disease and changing in order the oscillation frequency of said oscillator (12) on the basis of said read information of frequencies, and said plurality of frequencies are at least two frequencies of 14, 16, 19, 21, 25, 27, 59, 61, 71, 73, 94, 96, 119, 121, 124, 126, 159, 161, 441, 447, 449, 464, 466, 499, 501, 599, 601, 624, 626, 659, 661, 665, 667, 689, 691, 699, 701, 724, 726, 727, 728, 729, 731, 739, 741, 769, 771, 775, 777, 786, 788, 789, 791, 799, 800, 801, 802, 803, 804, 805, 831, 839, 874, 876, 879, 881, 884, 886, 891, 1499, 1501, 1549, 1551, 1559, 1561, 1569, 1571, 1599, 1601, 1799, 1801, 1839, 1841, 1849, 1851, 1899, 1901, 1997, 1999, 2001, 2007, 2009, 2051, 2099, 2101, 2121, 2126, 2127, 2128, 2129, 2131, 2488, 2489, 2490, 2491, 2999, 3001, 4999, 5001, 9999 and 10001 Hz.

56. A wave therapeutic apparatus (10), (40), (60) or (70) according to claim 55, claim 55, wherein said frequencies for a basic therapy prior to treatment of each disease are set at 19, 61, 96, 124, 667, 726, 741, 786, 791, 879 and 10001 Hz.

57. A wave therapeutic apparatus (10), (40), (60) or (70) according to claim 55 or 56, wherein said frequencies are selected in the following manner for each disease and said memory section (22) memorizes information of at least two frequencies of a plurality of frequencies selected for at least one kind of disease from among the following diseases; Abscess, tumor; 19, 21, 59, 73, 94, 126, 665, 728, 739, 788, 789, 881, stomachache; 879, 4999, 5001, 9999, 10001, acidosis; 19, 61, 71, 96, 124, 667, 726, 741, 786, 791, 879, 10001, pimple; 665, 728, 739, 788, 789, 881, 4999, actinomycosis; 19, 61, 71, 96, 124, 667, 726, 741, 786, 791, 879, 891, megalgia; 879, 9999, 10001, adenoids; 19, 61, 71, 96, 124, 667, 726, 741, 786, 791, 799, 881, adhesion; 665, 728, 739, 788, 791, 881, 4999, acquired immunodeficiency syndrome; 21, 59, 73, 94, 99, 121, 126, 447, 449, 464, 466, 499, 599, 626, 659, 667, 728, 739, 777, 788, 791, 799, 802, 805, 881, 1499, 1549, 1571, 1601, 1799, 1839, 1999, 2001, 2009, 2128, 2488, 2489, 2490, 2491, 4999, 9999, alcoholism; 665, 726, 741, 786, 791, 881, 9999, 10001, allergy; 667, 726, 741, 786, 791, 879, 4999, 5001, alopecia (hair loss); 665, 728, 741, 786, 791, 879, 9999, 10001, amenorrhea (unsuccessful memses); 665, 728, 741, 788, 791, 881, 9999, 10001, anemia; 19, 61, 96, 124, 667, 726, 741, 786, 791, 879, 4999, 10001, aneurysm; 19, 21, 61, 71, 94, 126, 4999, 5001, anus (pruritus ani); 21, 59, 73, 94, 124, 726, 788, 791, 879, 9999, 10001, spleen ulceration, anthrax (infectious disease of cattle); 665, 728, 739, 788, 791, 879, disinfection, sterilization; 665, 726, 741, 786, 789, 881, 5001, appendicitis, cecitis; 667, 728, 741, 788, 791, 881, anorexia; 665, 726, 739, 786, 789, 879, 10001, AIDS-related syndrome; 626, 661, arterial sclerosis; 21, 61, 73, 95, 124, 665, 726, 741, 788, 791, 881, 4999, 9999, artery (stimulate); 665, 728, 741, 788, 791, 801, 879, 9999, 10001, arteriosclerosis; 21, 61, 71, 96, 124, 665, 728, 741, 788, 791, 881, 4999, 5001, 9999, 10001, arthritis; 19, 21, 59, 71, 94, 126, 667, 726, 739, 786, 791, 801, 881, 1501, 1841, 1999, 2001, 2007, 2126, 4999, 5001, 9999, 10001, ataxia (muscle); 665, 726, 739, 788, 791, 881, 4999, 5001, 9999, 10001, athlete's foot; 21, 59, 73, 96, 124, 665, 726, 741, 786, 791, 879, 5001, asthma; 667, 728, 741, 788, 789, 881, star-shaped cerebral or spinal cells; 665, 728, 741, 786, 789, 879, 1999, 2001, 2007, 2009, 2126, 2128, autointoxication; 665, 726, 739, 788, 791, 879, 9999, 10001, rod virus; 665, 726, 739, 786, 789, 801, 802, 804, 5001, backache; 667, 728, 741, 788, 791, 881, 9999, 10001, respiratory insufficiency; 19, 21, 61, 73, 96, 126, 4999, 5001, irritability (irritable); 667, 726, 741, 786, 789, 881, 5001, 9999, 10001, fire blister, water blister; 19, 61, 73, 96, 126, 667, 728, 739, 879, water blister, bulla; 9999, blood disease; 665, 728, 739, 786, 791, 881, hypotension; 19, 61, 96, 124, 667, 726, 741, 786, 791, 879, 10001, tumor, eruption; 19, 21, 59, 71, 94, 124, 667, 728, 739, 786, 791, 879, tumor (rash, contagion); 19, 21, 59, 73, 96, 126, 667, 728, 741, 788, 789, 881, 4999, 5001, bone (crack, fracture); 19, 61, 96, 124, 667, 726, 741, 786, 791, 879, 10001, tumor of breast; 2007, 2127, 2129, region of chest; 19, 61, 96, 124, 667, 726, 741, 786, 791, 879, 4999, 10001, respiration; 19, 61, 96, 124, 667, 726, 741, 786, 791, 879, 5001, 10001, Bright's disease (most dangerous nephritis), nephritis; 667, 726, 739, 788, 791, 801, 879, pneumonia; 665, 728, 741, 777, 791, 881, bronchitis; 667, 728, 741, 879, bruise, cut, contusion; 667, 726, 741, 791, 881, 9999, 10001, bubonic plague, contagious disease; 19, 61, 73, 94, 124, 499, 501, 4999, pain of hallux valgus; 19, 21, 61, 73, 94, 124, 667, 726, 739, 788, 791, 4999, 5001, burn (radiant heat); 2126, 9999, 10001, burn (heat); 19, 61, 96, 124, 667, 726, 741, 786, 791, 879, 10001, bursitis; 665, 726, 739, 786, 791, 881, butterfly-shaped erythematous lupus; 665, 728, 739, 775, 777, 788, 791, 1841, 1849, cancer (sarcoma); 1999, 2001, 2007, 2009, 2126, 2128, cancer (generally, for prevention); 1997, 1999, cancer (inside, outside); 2126, cancer (leukemia); 19, 61, 96, 124, 667, 726, 741, 786, 791, 879, 2128, 10001, noma; 19, 59, 73, 96, 124, 665, 728, 741, 788, 791, 801, 881, 4999, 5001, mycosis fungoides, cavernous hemangioma, cutaneous disease of fish; 466, 2128, pimple, eruption; 21, 61, 73, 94, 126, 667, 728, 739, 788, 791, 881, 4999, 5001, cancer; 2121, 2126, 2131, heart disease (sedative effect); 665, 728, 739, 786, 789, 881, 4999, 5000, 9999, 10001, cataract; 667, 726, 741, 788, 791, 879, 4999, 5001, 9999, 10001, catarrh (inflammation of nasal mucous membrane); 19, 21, 59, 73, 96, 124, 665, 726, 741, 788, 789, 879, cerebral infantile paralysis; 665, 726, 739, 788, 791, 881, 9999, 10001, cerebrospinal meningitis; 667, 728, 741, 786, 789, 879, 9999, 10000, gland of neck (wen, swelling); 667, 728, 741, 786, 789, 879, 4999, 5001, cervicitis; 19, 59, 73, 96, 124, 665, 728, 741, 788, 791, 879, chicken pox, 19, 21, 61, 71, 94, 126, 667, 728, 739, 786, 789, 881, chilblains, frostbite; 19, 21, 59, 73, 96, 126, 4999, 5001, psychomatic disorder; 65, 728, 881, poor circulation (foot); 19, 21, 61, 73, 94, 124, 4999, 5001, poor circulation (hand); 19, 21, 59, 71, 96, 126, 4999, 5001, cold, cough; 665, 727, 729, 741, 788, 791, 801, 881, 4999, 5001, 9999, 10001, cold (head); 665, 727, 729, 739, 786, 789, 881, 4999, 5001, stomachache; 19, 61, 73, 96, 124, 667, 728, 739, 788, 789, 791, 799, 801, 881, colitis (mucosa of colon); 21, 59, 71, 94, 126, 665, 726, 741, 786, 789, 799, 801, 881, 9999, 10001, conjunctivitis (expansion of eyelid); 665, 726, 727, 729, 741, 788, 789, 801, 881, constipation; 19, 59, 73, 96, 126, 667, 728, 741, 786, 789, 791, 799, 801, 881, contraction of swelling, oozing of pus; 21, 61, 71, 94, 124, 665, 726, 788, 791, 881, 9999, 10001, spasm, convulsion; 665, 726, 739, 786, 791, 879, 4999, 9999, 10001, corn; 19, 21, 61, 71, 94, 126, 667, 726, 741, 788, 791, 879, 4999, 9999, 10001, coryza; 667, 726, 739, 788, 791, 881, costalgia; 667, 728, 739, 788, 791, 879, 5001, 9999, 10001, convulsion, leg cramp; 665, 726, 741, 788, 789, 881, 4999, 9999, 10001, cut (speed remedy); 19, 21, 59, 73, 96, 126, 667, 728, 741, 788, 791, 881, 4999, 5001, 9999, cystitis; 21, 61, 71, 94, 126, 665, 739, 788, 791, 799, 801, 881, 4999, 9999, 10001, dandruff; 21, 61, 71, 94, 126, 667, 728, 741, 788, 791, 881, 4999, 5001, deafness; 19, 21, 59, 73, 96, 126, 667, 739, 788, 789, 799, 801, 881, 4999, 9999, 10001, discouragement, melancholy; 9999, detoxification; 19, 61, 71, 94, 126, diabetes; 21, 59, 73, 94, 126, 665, 728, 786, 791, 799, 881, 4999, 9999, 10001, diarrhea (dysentery); 665, 728, 739, 788, 789, 801, 879, 4999, 5001, digestive power; 667, 726, 741, 786, 791, 879, 4999, 5001, diphtheria; 19, 21, 61, 71, 96, 124, 667, 726, 728, 739, 786, 788, 791, 879, 881, swelled organ; 21, 59, 73, 94, 126, 665, 728, 739, 788, 789, 881, 9999, 10001, swelled stomach; 667, 726, 741, 786, 791, 799, 801, 879, 4999, 5001, vertigo; 19, 21, 61, 71, 96, 124, 9999, 10001, edema; 665, 728, 786, 791, 9999, 10001, medicinal poisoning; 19, 21, 59, 73, 94, 126, 665, 728, 739, 788, 789, 881, 4999, 9999, 10001, duodenal ulcer; 667, 726, 728, 741, 786, 788, 791, 879, 881, 9999, 10001, dysmenorrhea (menorrhalgia); 665, 726, 728, 739, 788, 789, 799, 879, 881, indigestion, dyspepsia; 667, 726, 741, 786, 791, 799, 801, 881, colon bacillus; 791, 798, 800, 801, 802, 803, 805, ear; 19, 21, 59, 73, 94, 126, 879, 881, 4999, 5001, 9999, eczema; 667, 726, 741, 1499, 1501, 1549, 1551, 4999, pulmonary edema; 665, 726, 728, 741, 786, 788, 789, 879, 881, expanded gland; 19, 61, 71, 96, 124, 667, 726, 741, 786, 791, 999, 10001, nocturnal enuresis; 667, 726, 741, 786, 791, 9999, 10001, epididymitis, epidiymitis; 19, 21, 59, 73, 94, 126, 665, 728, 739, 788, 789, 881, 1499, 1501, epilepsy; 19, 21, 61, 71, 96, 119, 121, 124, 728, 739, 788, 789, 879, EB virus; 464, 466, 659, 661, 667, 726, 741, 786, 791, 879, 1999, 2001, 2007, 2126, 2128, erysipelas (cutaneous inflammation); 21, 59, 73, 94, 126, 599, 601, 661, 667, 728, 741, 788, 791, 1997, 1999, 2001, 2009, gullet; 665, 728, 741, 788, 791, 881, auditory tube, nose, ear; 19, 21, 61, 71, 96, 124, 667, 726, 741, 786, 791, 799, 801, 881, eyestrain; 728, 788, 879, eye (whole); 19, 21, 61, 73, 94, 126, 4999, 5001, 9999, 10001, facial paralysis; 665, 726, 739, 788, 881, 4999, 5001, 9999, 10001, facial spasm; 667, 728, 741, 786, 791, 879, 9999, 10001, fainting, swoon; 19, 21, 61, 71, 94, 126, 665, 728, 739, 788, 789, 881, 4999, 5001, fascia, muscle sheath; 19, 21, 59, 73, 96, 124, 667, 726, 741, 786, 791, 879, 4999, 5001, fatigue; 665, 739, 791, 1841, 1999, 9999, 10001, fever (in general); 19, 21, 59, 71, 96, 126, 665, 728, 741, 788, 791, 881, 4999, 5001, crack of rectum; 19, 21, 61, 73, 94, 124, 667, 726, 739, 786, 789, 879, 9999, 10001, fistulation, fistula (rectum ulcer), 667, 726, 741, 788, 791, 879, gas in the stomach and intestines; 667, 728, 741, 788, 791, 799, 801, 881, 4999, 5001, influenza; 19, 61, 71, 94, 124, 667, 728, 741, 786, 791, 799, 801, 881, sitotoxism; 667, 726, 739, 788, 791, 879, 9999, 10001, foot (ordinary injury); 665, 728, 739, 788, 791, 881, 9999, 10001, frostbite; 665, 728, 741, 788, 791, 879, 4999, 5001, gallstone; 19, 21, 61, 71, 94, 124, 667, 728, 741, 788, 789, 881, 4999, gallbladder; 19, 21, 61, 71, 94, 124, 667, 728, 741, 788, 789, 881, 4999, 5001, gangrene; 19, 21, 667, 726, 728, 741, 786, 788, 789, 879, 881, 4999, gastritis; 19, 21, 61, 73, 96, 124, 667, 728, 741, 788, 789, 881, 4999, 5001, all glands; 19, 21, 61, 73, 96, 126, 728, 741, 788, 789, 879, 9999, 10001, glaucoma; 19, 61, 96, 124, 667, 726, 741, 786, 791, 879, 1601, 10001, goiter; 19, 21, 59, 71, 96, 126, 667, 728, 741, 788, 791, 881, 4999, 5001, 9999, 10001, genital gland (inflammation); 667, 726, 728, 741, 786, 788, 791, 879, 881, 4999, gonorrhea, 599, 601, 659, 661, 667, 699, 701, 728, 741, 788, 789, 881, 4999, gout, 19, 21, 61, 71, 94, 124, 667, 728, 741, 788, 789, 881, 4999, 9999, 10001, gravel (deposits in urine); 667, 728, 739, 786, 789, 879, 4999, 5001, gingival inflammation; 19, 21, 61, 73, 94, 124, 791, 799, 801, 881, 4999, 5001, 9999, 10001, damaged hair; 19, 21, 59, 71, 94, 126, 667, 728, 741, 791, 801, 881, 9999, 10001, hallucination, 19, 21, 61, 73, 96, 124, 665, 726, 741, 788, 881, 4999, 5001, 9999, hangover; 19, 61, 96, 124, 667, 726, 741, 786, 791, 879, 9999, 10001, hay fever; 665, 728, 741, 788, 791, 881, 4999, 5001, head (oppression); 19, 21, 61, 73, 96, 124, 665, 726, 739, 788, 791, 879, 4999, 5001, headache; 19, 21, 61, 73, 96, 124, 667, 726, 741, 788, 791, 881, 9999, 10001, heart (in general); 665, 728, 741, 788, 791, 881, 4999, 5001, 9999, hemorrhage; 801, 9999, hemorrhoid; 19, 21, 59, 71, 96, 126, 667, 728, 741, 789, 799, 801, 879, 881, hepatitis (inflammation of liver); 665, 726, 727, 729, 741, 791, 801, 879, 881, hernia of an intervertebral disk; 665, 728, 741, 788, 791, 9999, 10001, hernia; 667, 726, 739, 788, 789, 4999, 5001, herpes (zoster blister); 665, 728, 741, 788, 879, 1549, 1551, 1841, 1849, 1851, 1899, 1901, 1997, 2001, 2007, hiccough; 19, 21, 59, 73, 94, 124, 9999, 10001, pain of hip; 19, 59, 71, 94, 124, 665, 728, 741, 788, 791, 881, 4999, 5001, urticaria; 667, 728, 741, 788, 791, 881, 1799, 1801, 4999, hoarse voice; 665, 726, 728, 741, 786, 788, 789, 879, 881, hot flash; 19, 61, 96, 124, 667, 726, 741, 786, 791, 879, 9999, 10001, edema; 667, 728, 741, 788, 791, 881, 9999, 10001, gastric hyperacidity; 19, 21, 61, 73, 96, 126, 667, 728, 741, 788, 791, 881, 9999, 10001, hypertension; 19, 21, 61, 73, 96, 126, 667, 728, 741, 788, 791, 881, 9999, 10001, hypochondriasis (melancholia); 19, 21, 61, 73, 96, 126, 667, 728, 741, 788, 791, 881, 9999, 10001, dyspnea, hypoxia; 667, 728, 741, 788, 791, 881, 9999, 10001, inflammation of colon; 19, 59, 71, 96, 126, 667, 728, 741, 788, 791, 799, 801, 881, asthenia, inertia; 19, 61, 96, 124, 667, 726, 741, 786, 791, 879, 9999, 10001, gigantism; 19, 61, 96, 124, 667, 726, 741, 786, 791, 879, 999910001, indigestion, dyspepsia; 665, 728, 741, 788, 791, 881, 4999, 5001, infantile paralysis; 667, 728, 741, 788, 791, 881, 1499, 1501, 1551, 1599, 1841, 1999, contagious disease; 19, 21, 726, 728, 729, 741, 788, 791, 881, inflammation of breast; 665, 728, 739, 786, 789, 881, 4999, 5001, influenza, influenza; 19, 21, 61, 73, 96, 124, 665, 726, 741, 788, 791, 799, 801, 879, 881, injury; 4999, 5001, 9999, sting of an insect; 665, 726, 728, 741, 788, 791, 879, 881, insomnia; 667, 728, 739, 788, 791, 881, 9999, 10001, intelligence, intellectuality (for improvement); 19, 21, 61, 73, 94, 124, 9999, 10001, intercostal neuralgia; 665, 728, 741, 788, 791, 799, 801, 881, 9999, 10001, intestines (inflammation); 667, 726, 741, 788, 789, 881, intestines (spasm); 665, 728, 741, 788, 791, 799, 801, 4999, 5001, intestines (in general); 665, 728, 741, 788, 789, 799, 801, 881, drunkenness, excitation; 19, 61, 96, 124, 667, 726, 741, 786, 791, 879, 9999, 10001, irritable, quick temper; 19, 21, 59, 73, 94, 124, 4999, 5001, 9999, 10001, urtication of anus; 667, 728, 741, 788, 789, 881, 4999, 5001, jaundice; 667, 728, 741, 788, 791, 881, 4999, 5001, joint (inflammation in general); 667, 728, 741, 788, 791, 881, 9999, 10001, kidney (general); 19, 21, 59, 71, 94, 124, 665, 728, 788, 791, 881, 9999, 10001, pain in knee; 21, 61, 71, 96, 126, 667, 728, 741, 788, 791, 799, 801, 881, 9999, promotion of secretion of breast milk; 19, 61, 96, 124, 667, 726, 741, 786, 791, 879, 4999, 10001, languidness, fatigue, weakness; 19, 21, 59, 71, 94, 124, 665, 728, 788, 791, 881, chronic diarrhea; 19, 61, 73, 96, 124, 667, 728, 741, 788, 791, 799, 801, 881, Hansen's disease; 599, 601, 667, 726, 739, 777, 791, 881, 9999, 10001, leukocyte; 19, 59, 73, 96, 126, 667, 728, 741, 4999, 5001, leukemia and cancer; 665, 728, 739, 786, 791, 779, 1999, 2001, 2009, 2126, 2128, abnormal secretion of white discharge from the vagina; 665, 726, 728, 741, 786, 788, 791, 879, 881, whole liver; 665, 726, 727, 729, 739, 786, 788, 789, 791, 881, motor ataxia; 667, 728, 741, 788, 791, 881, 9999, 10001, lumbago; 667, 728, 741, 788, 791, 881, 9999, 10001, crooked waist vertebra; 667, 728, 741, 788, 791, 881, 9999, 10001, lupus; 1499, 1549, 1551, 1601, 1841, 1997, whole lymphatic tissue; 665, 728, 741, 788, 791, 881, 4999, 5001, malaria; 19, 21, 59, 71, 94, 126, measles; 665, 726, 727, 729, 741, 786, 788, 791, 879, 881, depression; 19, 61, 96, 124, 667, 726, 741, 786, 791, 879, 4999, 10001, memory; 19, 21, 59, 71, 94, 124, 9999, 10001, Meniere's disease; 19, 21, 61, 71, 96, 126, 667, 728, 741, 788, 791, 879, 881, 4999, 5001, 9999, 10001, meningitis, meningoencephalitis; 19, 21, 61, 73, 96, 126, 4999, 5001, missed period; 665, 728, 741, 788, 791, 881, 9999, 10001, menorrhalgia; 19, 25, 27, 61, 73, 96, 126, mental retardation; 19, 21, 59, 73, 96, 124, 9999, 10001, migraine; 19, 21, 665, 728, 741, 879, 791, 881, 4999, 5001, Down's syndrome; 21, 4999, stomatitis; 19, 21, 59, 71, 94, 124, 665, 726, 741, 788, 791, 881, 4999, disease of evacuation; 19, 9999, multiple sclerosis; 19, 59, 71, 94, 124, 665, 726, 739, 788, 789, 879, 4999, 5001, epidemic parotiditis; 665, 726, 727, 729, 741, 786, 788, 791, 879, 881, muscles (restoration); 19, 61, 96, 124, 667, 726, 741, 786, 791, 879, 4999, 10001, muscular dystrophy; 665, 726, 739, 788, 791, 881, 4999, 5001, nausea, vomiturition; 667, 728, 741, 788, 791, 881, 4999, 5001, whole neck; 19, 59, 71, 96, 124, 667, 728, 741, 788, 791, 881, 4999, 5001, nephritis; 19, 21, 61, 73, 96, 126, 667, 728, 741, 788, 791, 799, 881, 9999, 10001, dental neuritis; 667, 728, 741, 788, 791, 881, 9999, 10001, erethism (sedative effect); 4999, neuralgia; 21, 61, 73, 96, 126, 667, 726, 741, 788, 879, 9999, 10001, nervous prostration (fatigue); 665, 726, 739, 786, 791, 881, 4999, 5001, neuritis; 665, 726, 739, 786, 791, 881, 9999, 10001, neurosis; 665, 726, 739, 786, 791, 881, 9999, 10001, nicotinism; 19, 61, 96, 124, 667, 726, 741, 786, 791, 879, 9999, 10001, nasal disorder; 665, 726, 728, 739, 786, 788, 791, 881, adiposis; 19, 61, 96, 124, 667, 726, 741, 786, 791, 879, 9999, 10001, occipital neuralgia; 19, 61, 73, 94, 124, 665, 726, 739, 788, 791, 881, 4999, 5001, testitis; 665, 728, 741, 788, 791, 799, 799, 801, 881, arthritis; 665, 728, 741, 788, 791, 881, 1499, 1501, 1551, 1601, 1839, 1999, osteomyelitis; 665, 728, 741, 788, 791, 881, 4999, 5001, whole ovary; 726, 788, 881, pain, ache; 665, 728, 739, 786, 789, 881, 1841, 1999, Parkinson's disease; 667, 726, 741, 791, 879, 1501, 1601, 1839, 1999, 2001, 4999, 5001, pancreas; 14, 16, 19, 61, 73, 94, 124, 665, 728, 739, 788, 791, 881, parasite; 19, 73, 96, 119, 121, 126, 439, 441, 447, 665, 726, 739, 786, 791, 799, 881, parathyroid; 665, 726, 728, 741, 786, 788, 791, 879, 881, whole pelvis; 19, 21, 61, 71, 96, 126, 659, 661, 665, 728, 741, 788, 791, 881, 1499, 1501, 1551, 1599, 1841, 1999, pericarditis; 665, 726, 728, 741, 786, 788, 791, 879, 881, periodontal disease; 665, 726, 728, 741, 786, 788, 791, 879, 881, tonic disease; 19, 21, 61, 71, 94, 119, 121, 124, 4999, laryngitis; 667, 726, 728, 741, 786, 788, 791, 879, 881, hemorrhoids; 19, 21, 61, 71, 94, 124, 788, 791, 799, 801, 879, 881, threadworm, parasite; 19, 21, 61, 73, 96, 119, 121, 124, 788, 791, 799, 801, placenta (afterbirth); 665, 726, 728, 741, 786, 788, 791, 879, 881, blood plasma, lymphoid plasma (cleaning); 19, 61, 96, 124, 667, 726, 741, 786, 791, 879, 4999, 10001, pleurisy, (pleura); 19, 21, 59, 71, 94, 124, 665, 726, 741, 789, 879, 4999, 5001, pneumonia; 19, 21, 71, 94, 124, 665, 726, 741, 769, 771, 775, 777, 788, 791, 879, 881, 4999, 5001, poison (drug), botulism, ptomaine toxication, narcotic; 9999, acute anterior poliomyelitis; 665, 728, 741, 788, 791, 879, 1499, 1501, 1551, 1601, 1839, 1999, polyp (nasal polyp); 1841, 1999, 2001, 2126, 2127, 2129, prostatitis; 665, 726, 741, 788, 791, 879, 4999, psoriasis; 19, 21, 61, 71, 94, 124, 665, 726, 739, 788, 791, 881, 4999, 5001, blepharoptosis; 665, 726, 739, 788, 791, 881, 4999, 9999, pyorrhea; 19, 21, 59, 71, 94, 124, 665, 726, 739, 788, 791, 4999, rabies, hydrophobia; 19, 21, 59, 71, 94, 119, 121, 126, 665, 728, 741, 788, 791, 879, rheumatism; 665, 728, 741, 788, 791, 879, 9999, 10001, rheumatism and arthritis; 19, 59, 71, 94, 124, 599, 659, 667, 728, 739, 788, 791, 801, 881, 1501, 1549, 1601, 1839, 1999, 2001, 2007, 2128, 2129, 4999, 9999, 10001, nasal catarrh; 19, 21, 61, 71, 96, 119, 121, 126, 667, 728, 741, 788, 881, rachitis; 19, 61, 96, 124, 667, 726, 741, 786, 791, 879, 4999, 10001, tinea, ringworm; 19, 21, 59, 71, 94, 119, 121, 124, 788, 791, 799, 801, sarcoma; 1997, 1999, 2001, 2009, 2099, 2101, 2126, 2127, scarlet fever; 665, 726, 727, 729, 739, 786, 788, 791, 879, 881, sciatic neuralgia; 19, 21, 59, 71, 94, 119, 121, 124, 665, 726, 739, 788, 791, 881, scorbutus; 19, 61, 96, 124, 667, 726, 741, 786, 791, 879, 4999, 10001, hemiplegia; 19, 21, 59, 71, 94, 126, 4999, 5001, zoster; 1501, 1549, 1551, 1601, 1839, 1999, 2001, sinus fistula; 19, 21, 59, 71, 96, 119, 121, 124, 665, 726, 739, 788, 789, 881, sinusitis; 665, 726, 728, 741, 786, 788, 791, 879, 881, cutis (hemorrhage); 786, 791, 799, 801, 4999, 5001, 9999, sleeping sickness; 19, 21, 59, 71, 96, 119, 121, 126, 667, 728, 741, 788, 791, 881, dislocation of an intervertebral disk; 665, 728, 739, 788, 789, 9999, 10, 001, variola, smallpox; 667, 726, 727, 729, 741, 786, 788, 791, 879, 881, smell (lack, deficiency); 19, 21, 59, 71, 96, 126, 9999, 10001, diseased smell; 665, 728, 739, 788, 791, 799, 801, sneeze; 665, 728, 739, 788, 789, 881, 9999, 10001, laryngitis; 665, 726, 727, 729, 739, 786, 788, 789, 879, 881, muscular spasm; 19, 21, 59, 71, 94, 124, 9999, 10001, unconscious spermatorrhea; 19, 21, 59, 71, 94, 124, 9999, 10001, spleen (hypertrophy); 19, 21, 61, 71, 94, 126, spondylitis; 788, 789, 799, 801, 879, 881, 1549, 1559, 1561, 1571, sprain, wrick in general; 19, 21, 59, 71, 94, 126, 4999, 5001, dysphemia; 19, 21, 59, 71, 96, 126, 665, 728, 741, 788, 791, 881, 9999, 10001, staphylococcus; 724, 726, 727, 728, 729, 731, 739, 788, 791, 881, infertility (prevention); 1839, 1999, 2001, 2007, 2009, 2126, 2128, 2129, 4999, 9999, gastospasm; 19, 21, 59, 71, 96, 126, 665, 726, 739, 788, 791, 881, 9999, 10001, calculus of kidney and gallbladder; 665, 728, 791, 801, 881, 9999, 10001, streptococcus; 667, 728, 739, 788, 791, 874, 876, 879, 881, 884, 886, paroxysm, apoplexy, cerebral apoplexy; 19, 21, 61, 71, 94, 126, 788, 791, 879, 4999, 9999, 10001, hordeolum; 19, 21, 61, 71, 94, 126, 788, 791, 879, 4999, 5001, 9999, 10001, sunstroke; 19, 21, 61, 71, 94, 126, 9999, 10001, adrenal stimulation; 19, 21, 61, 71, 94, 126, 4999, 5001, surgery; 665, 726, 728, 741, 786, 788, 791, 879, 881, 5001, tumor (under malleolus); 19, 21, 59, 71, 96, 126, 665, 726, 739, 788, 791, 881, 4999, 9999, 10001, syndrome (in general); 19, 21, 59, 71, 96, 126, 665, 726, 739, 788, 791, 881, 9999, 10001, syphilis; 19, 21, 61, 73, 96, 124, 599, 601, 624, 626, 667, 699, 701, 728, 741, 788, 791, 881, 9999, gustatory anesthesia; 19, 21, 61, 73, 96, 126, 9999, 10001, tetanus; 599, 601, 661, 667, 701, 728, 741, 788, 791, 881, thalamus (part of diencephalon); 19, 21, 61, 71, 94, 126, 4999, 5001, thrombophlebitis; 1499, 1501, 1551, 1601, thrombosis; 19, 21, 61, 71, 96, 126, 791, 799, 801, 1499, 1501, 4999, 5001, thrush; 665, 728, 741, 788, 791, 881, thymus (in general); 19, 21, 59, 71, 94, 126, 667, 728, 741, 788, 791, 881, 4999, 5001, thyroid gland; 19, 59, 71, 96, 124, 159, 161, stimulation of tissue cells; 665, 726, 739, 788, 791, 881, 1841, 1999, 2001, 2999, 3001, 4999, 5001, tonsillitis; 19, 21, 61, 73, 96, 126, 667, 728, 741, 788, 799, 801, 881, 5001, toothache; 19, 21, 667, 728, 741, 788, 791, 881, 4999, poison reaction; 19, 61, 73, 96, 124, trachoma (inflammation of eyes); 726, 788, 881, mental trauma; 665, 728, 741, 786, 791, 881, 5001, 9999, 10001, tuberculosis; 19, 21, 61, 71, 94, 126, 667, 728, 741, 788, 791, 799, 801, 1499, 1501, 1549, 1551, 1599, 1601, tumor in general; 1841, 1997, 1999, 2007, 2009, 2126, 2128, 2129, typhoid; 19, 21, 61, 73, 96, 126, 667, 689, 691, 1499, 1501, 1551, 1569, 1571, 1601, ulcer; 726, 777, 788, 881, unconsciousness, stun; 19, 21, 801, 5001, inflammation in urethra in general; 667, 728, 741, 788, 791, 879, 881, urtication; 1841, 1999, 2001, 2007, 2009, virus disease; 777, 788, 801, 831, 839, 881, 1571, 1999, 2051, 2488, 2491, 4999, verruca; 667, 728, 786, 788, 1841, 1999, 2001, 2007, 2009, 2126, 2128, 2129, whiplash; 19, 21, 61, 73, 96, 126, 9999, 10001, yellow fever; 19, 21, 61, 73, 96, 879, 881, 9999, 10001.

58. A wave therapeutic apparatus (10), (40), (60) or (70) according to claim 57, wherein said frequencies of electric current to be passed through said living body (P) are in a range of said selected frequencies plus or minus 3 Hz.

59. A wave therapeutic apparatus (10), (40), (60) or (70) according to claim 55, comprising said low-frequency electric current applying apparatus (10) and said acoustic wave applying apparatus, wherein;

at least one of the therapeutic electrode (14) and the inactive electrode (16) in said low-frequency electric current applying apparatus (10) functions also as an acoustic wave oscillator in said acoustic wave applying apparatus (60).

60. A wave therapeutic apparatus (10), (40), (60) or (70) according to claim 55, wherein said frequency selection controller (84) outputs said frequency selection signal to said frequency selecting device through a wire or wireless communication circuit (86).

\* \* \* \* \*